(12) United States Patent
Mizoguchi et al.

(10) Patent No.: US 11,896,680 B2
(45) Date of Patent: Feb. 13, 2024

(54) DETECTION METHOD

(71) Applicant: Mie University, Tsu (JP)

(72) Inventors: Akira Mizoguchi, Tsu (JP); Koji Tanaka, Tsu (JP); Kazushi Kimura, Tsu (JP); Tetsuya Nosaka, Tsu (JP); Kyosuke Tanaka, Tsu (JP); Shujie Wang, Tsu (JP); Aika Kaito, Tsu (JP); Kousyoku Sai, Tsu (JP); Yuji Toiyama, Tsu (JP); Hidemasa Goto, Tsu (JP); Masahiko Sugimoto, Tsu (JP); Yuuhei Nishimura, Tsu (JP)

(73) Assignee: MIE University, Mie (JP)

( * ) Notice: Subject to any disclaimer, the term of this patent is extended or adjusted under 35 U.S.C. 154(b) by 556 days.

(21) Appl. No.: 16/762,906

(22) PCT Filed: Nov. 27, 2018

(86) PCT No.: PCT/JP2018/043636
§ 371 (c)(1),
(2) Date: May 8, 2020

(87) PCT Pub. No.: WO2019/107370
PCT Pub. Date: Jun. 6, 2019

(65) Prior Publication Data
US 2021/0169315 A1 Jun. 10, 2021

(30) Foreign Application Priority Data
Nov. 28, 2017 (JP) ................. 2017-228477

(51) Int. Cl.
*A61K 49/00* (2006.01)
*A61B 1/00* (2006.01)
*A61B 1/04* (2006.01)
*A61B 1/06* (2006.01)
*A61B 1/31* (2006.01)
(Continued)

(52) U.S. Cl.
CPC ........ *A61K 49/006* (2013.01); *A61B 1/00055* (2013.01); *A61B 1/000094* (2022.02); *A61B 1/043* (2013.01); *A61B 1/063* (2013.01); *A61B 1/31* (2013.01); *A61B 5/0071* (2013.01); *G01N 21/6486* (2013.01)

(58) Field of Classification Search
CPC ............ A61K 49/006; A61B 1/000094; A61B 1/00055; A61B 1/043; A61B 1/063; A61B 1/31; A61B 5/0071; A61B 1/00006; A61B 1/00172; A61B 1/045; G01N 21/6486; G01N 21/6458; G01N 2021/6439
See application file for complete search history.

(56) References Cited

U.S. PATENT DOCUMENTS

| 2004/0191839 A1* | 9/2004 | Tokunaga | ............ C12N 15/873 435/7.2 |
| 2007/0077202 A1* | 4/2007 | Yamamoto | ........... A61K 49/006 424/9.1 |

(Continued)

*Primary Examiner* — Tom Y Lu
(74) *Attorney, Agent, or Firm* — Gavrilovich, Dodd & Lindsey LLP

(57) ABSTRACT

Provided is a vital stain inspection method for distinguishing between cancer cells and normal cells within a lumen, or on the serous membrane side of an organ, by means of laser irradiation after organ tissue has been stained by curcumin, Red #3 or Red #106, which are edible color dyes.

19 Claims, 41 Drawing Sheets

(51) Int. Cl.
*G01N 21/64* (2006.01)
*A61B 5/00* (2006.01)

(56) References Cited

U.S. PATENT DOCUMENTS

| | | | | |
|---|---|---|---|---|
| 2008/0045796 | A1* | 2/2008 | Yamamoto | A61K 49/0023 424/9.6 |
| 2009/0215038 | A1* | 8/2009 | Al-Mulla | G01N 33/57407 435/6.14 |
| 2013/0087724 | A1* | 4/2013 | Kuroda | G01B 9/02024 250/550 |
| 2016/0041100 | A1* | 2/2016 | Mizoguchi | C09B 23/04 549/33 |

\* cited by examiner

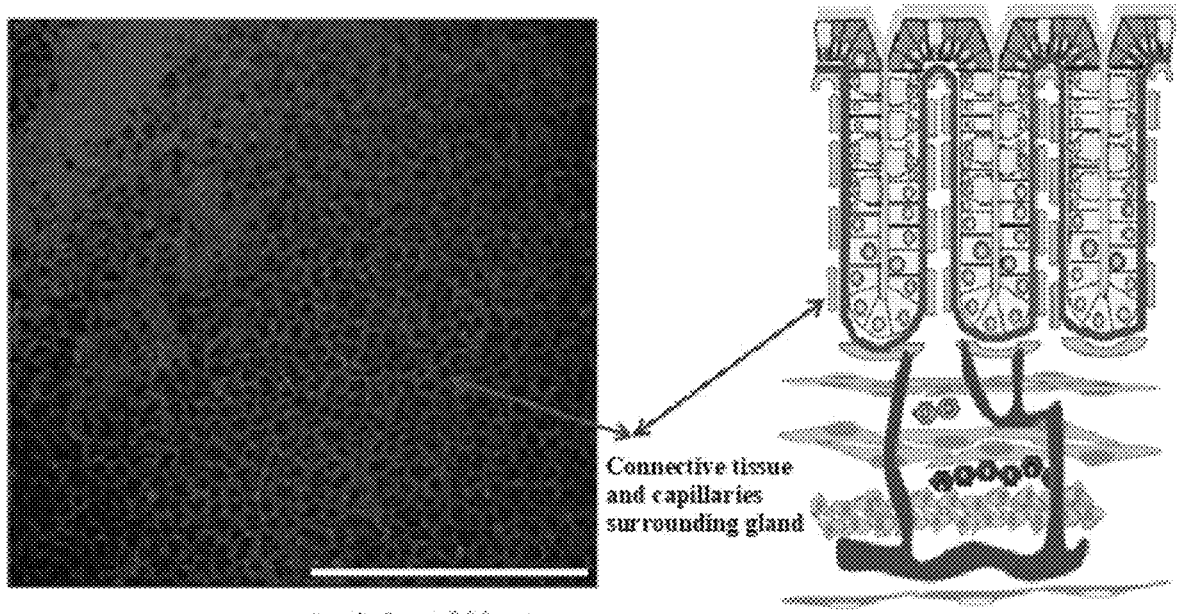
Scale bar : 500 μm
Since Red #106 stains
connective tissue and
capillaries surrounding
gland, a mesh-like
glandular structure can
be visualized by the negative
center and the surroundings
dyed red.
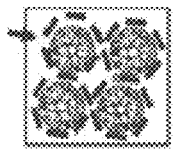
Normal tissue
Since the regular distribution pattern
of glandular structure and crypt structure
continues, it can be confirmed as normal.
FIG. 5G Cancer cells invading a smooth muscle layer and its interior Scale Bar: 200 μm

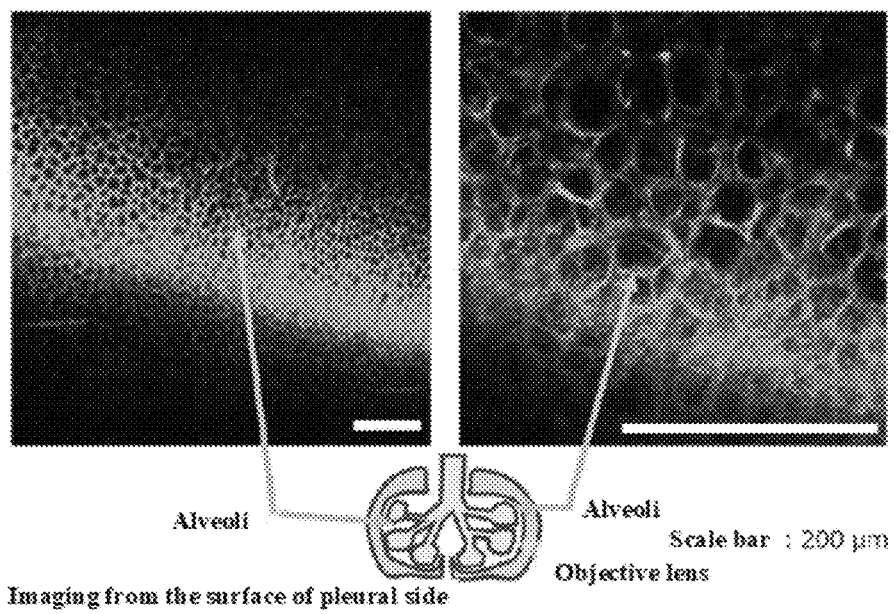
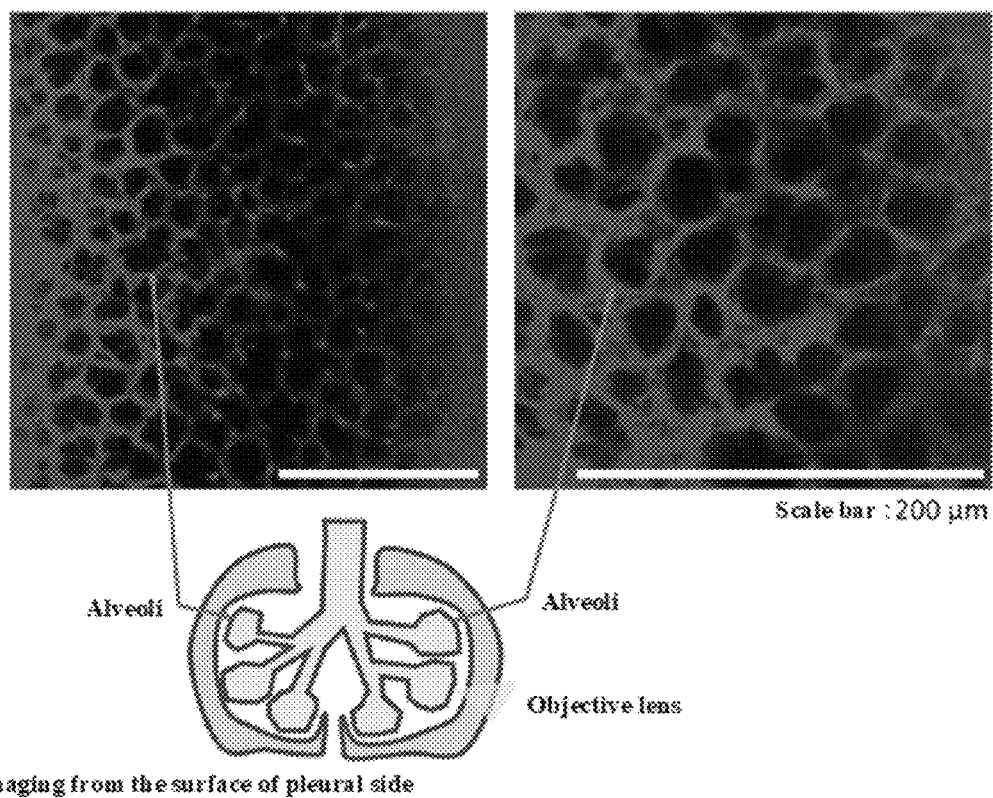
FIG. 13

Vital staining of tongue tip with curcumin
Small taste buds in tongue tip
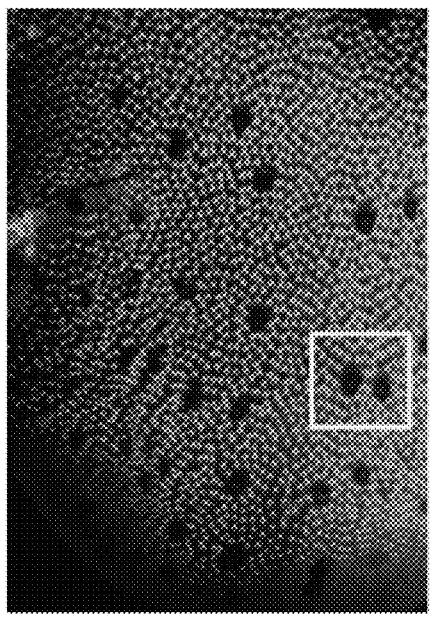
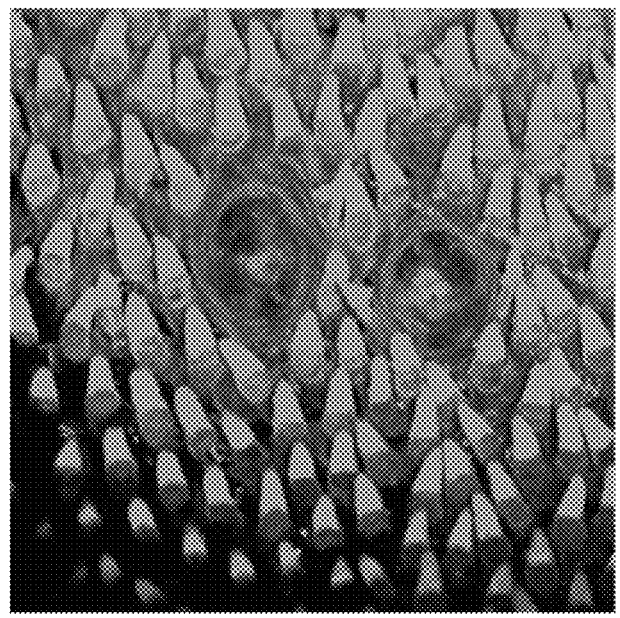
FIG. 22

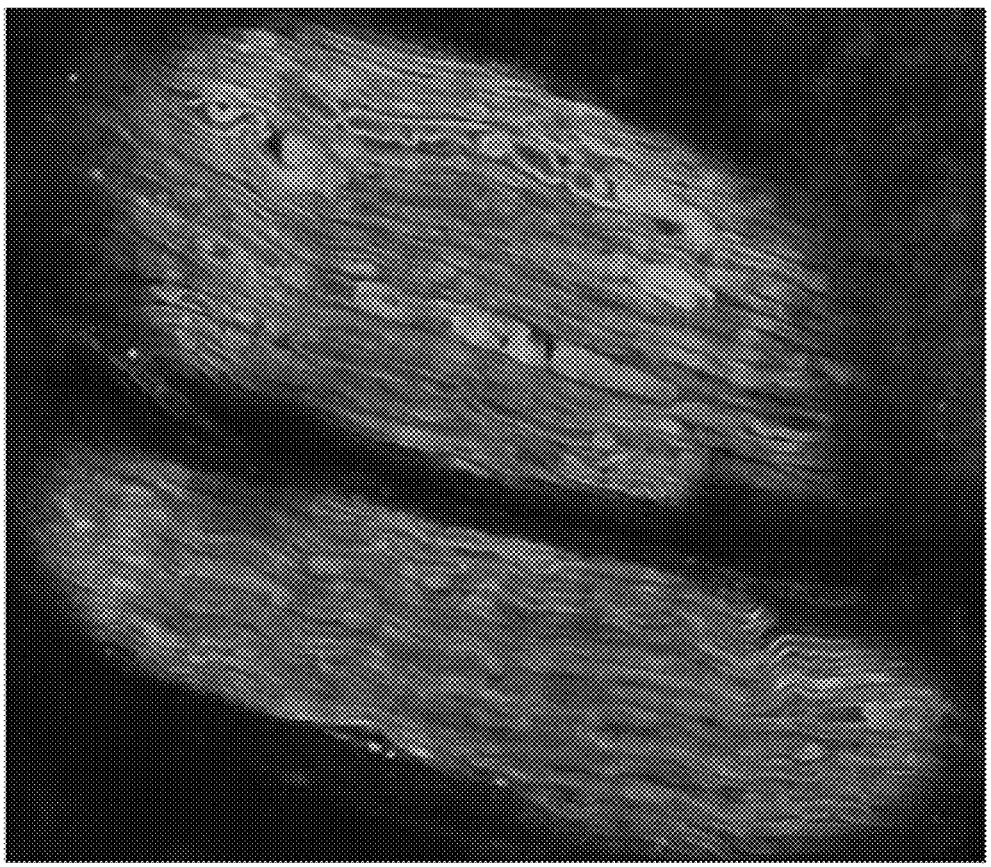
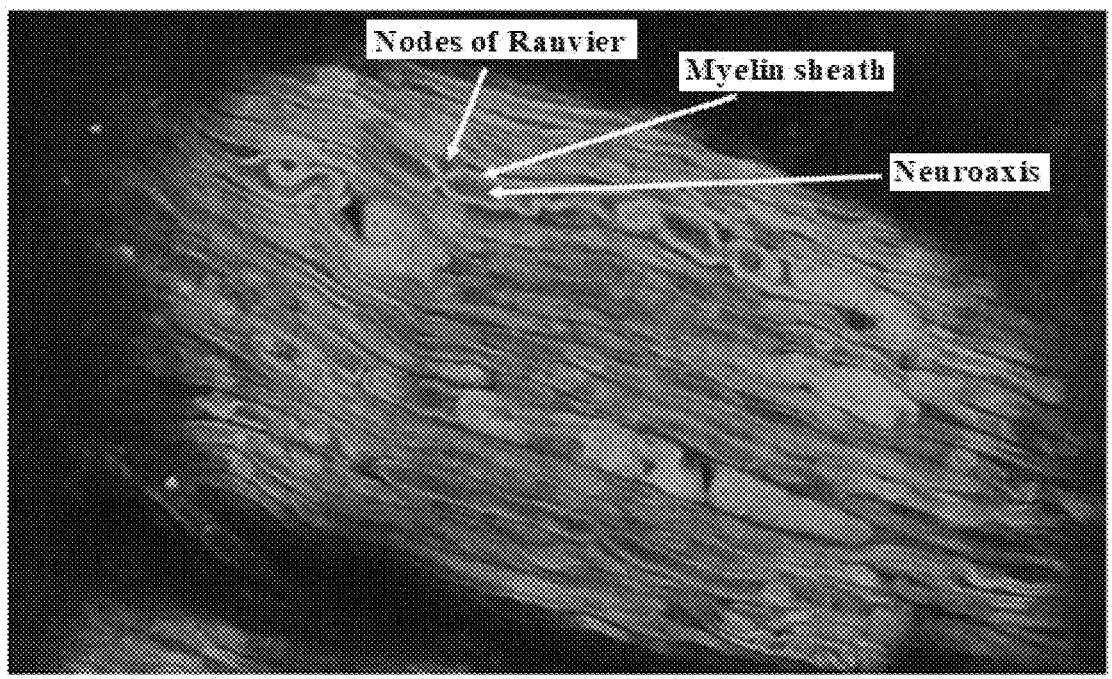
FIG. 25

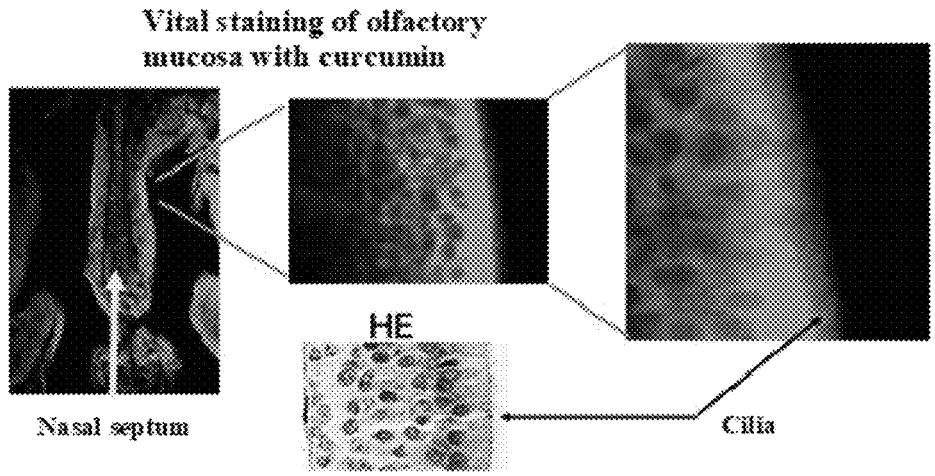
Cytoplasm of olfactory receptor neurons and cilia with odor receptors are stained positively by curcumin. The nuclei are not stained and can be visualized as a black negative image.
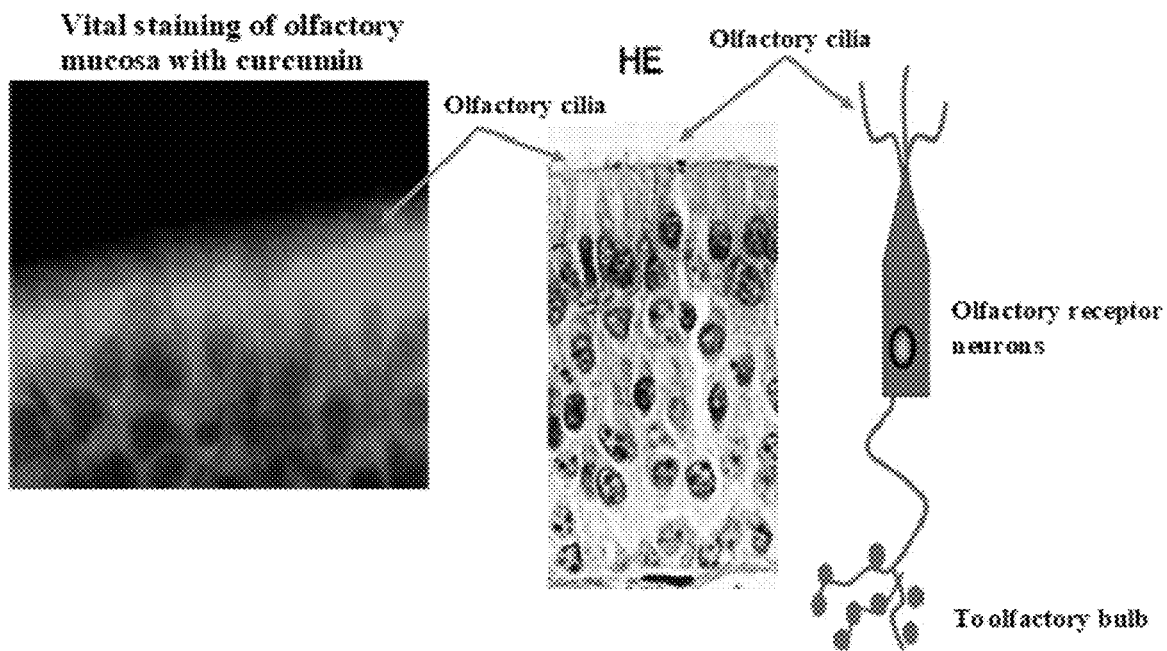
FIG. 26

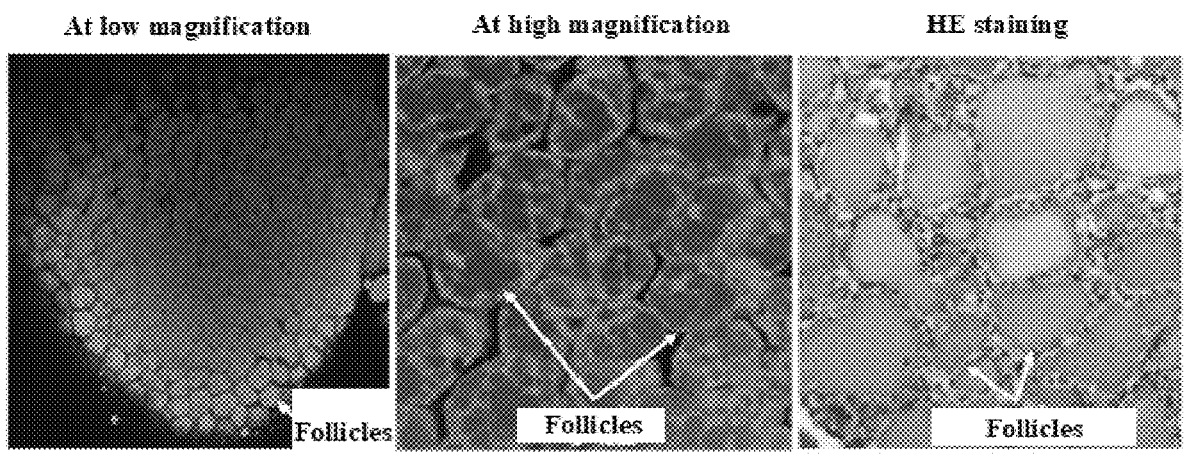

Vital staining of thyroid mucosa with curcumin

At low magnification | At high magnification | HE staining

Thyroid is formed by spherical follicles of various sizes. These follicles are bordered by a monolayer of squamous or cubic epithelium, and are filled with colloid that is evenly tained with hematoxylin and eosin in lumen. The periphery of vesicle s is surrounded by a dense capillary network.

FIG. 27

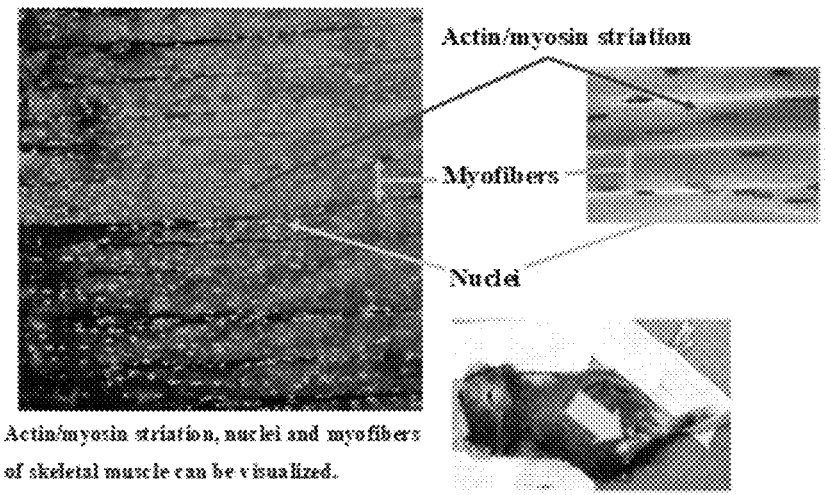
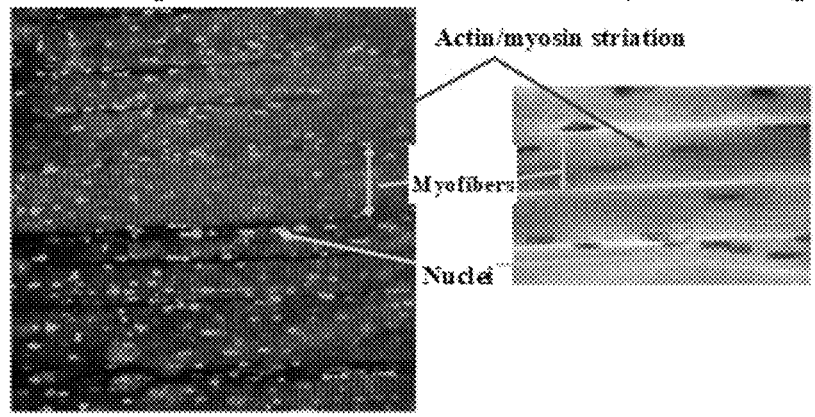
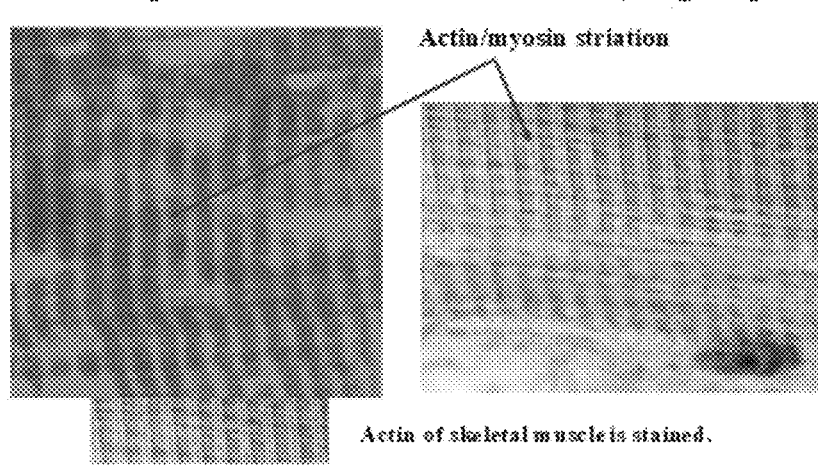
FIG. 28

Many cells with large bright nuclei can be observed in bright center. These are reticulum cells and large lymphocytes which are undergoing cell division. The dark shells have a structure in which small lymphocytes proliferating in the bright center accumulate around the bright center
Vital staining of lymph node
HE staining
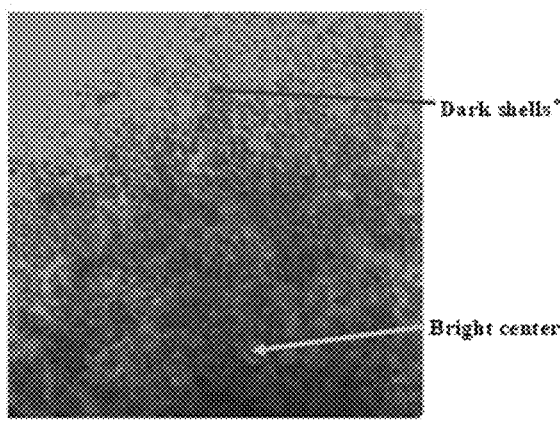
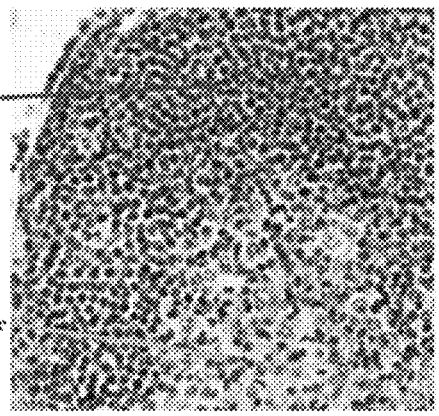
Dark shells
Bright center
FIG. 29

DETECTION METHOD

CROSS REFERENCE TO RELATED APPLICATIONS

This application is a U.S. National Phase Application filed under 35 U.S.C. § 371 and claims priority to International Application No. PCT/JP2018/043636, filed Nov. 27, 2018, which application claims priority under 35 U.S.C. § 119 to Japanese Application No. 2017-228477, filed Nov. 28, 2017, the disclosures of which are incorporated herein by reference.

TECHNICAL FIELD

The present invention relates to vital staining test methods and tissue visualization methods for distinguishing cancer cells from normal cells in organs by laser irradiation after vital staining tissues of organs with edible color dyes.

BACKGROUND ART

Cancer is currently the leading cause of death in Japan, with one in two people suffering from cancer and one in four dying from cancer. Moreover, the number of deaths from cancer is still increasing, and reducing the number of deaths from cancer is a public desire. The basic strategy to reduce cancer deaths is considered to be early detection of cancers. However, there is a limit in current test methods using endoscopy, since it is difficult to be detect cancers with a diameter of less than 10~20 mm. Therefore, at present, most cancer patients are treated by surgical resection of cancers. Accordingly, there is an urgent need to develop a rapid supportive technology for making decisions before and during surgery.

The goal of surgical resection of cancers is to simultaneously achieve the extremely difficult goals of completely removing cancer cells as much as possible and maximizing preservation of organ function after removal of lesion. Great improvements in surgical technics and efforts have been made to achieve this very difficult goal. One of the key points to improve a result of surgical cancer treatment has been rapid pathological diagnosis. It will be of great help if a surgeon can accurately ascertain the extent to which cancer cells have invaded or metastasized in an organ that has developed a cancer and its surrounding organs, as well as lymph nodes and blood vessels at pathological diagnosis level before and during surgery.

A method has been reported (Patent Literature 1) for distinguishing cancer cells from normal cells with fibers such as a laser microscope endoscope from lumen surface after staining digestive tract from luminal surface in vivo with edible color dyes, such as curcumin, sulfuretin, Red #3 and Red #106, etc. Meanwhile, there are few effective methods for distinguishing cancer cells from normal cells from serosal surface or lumen of digestive tract or the like before or during surgery. Accordingly, there is a strong demand for developing such methods.

PRIOR ART LITERATURE

Patent Literature

1. WO2014/157703

SUMMARY OF THE INVENTION

Problems to be Solved by the Invention

With the introduction of a robot for endoscopic surgery in thoracic cavity or abdominal cavity, less invasive surgery is performed without laparotomy, and the burden on patients is greatly reduced. On the other hand, in case of cancers, in order to avoid recurrence due to micro-invasion, even if a robot for endoscopic surgery in thoracic cavity or abdominal cavity is used, a resection site has to be extensive. For reducing the burden on patients, it is necessary to reduce the resection extent. Since a surgery is basically performed from the serosal side of an organ, before and during surgery, if it is possible to predict the extent of invasion of cancer cells from the serosal side before resection of an affected part, the resection extent can be reduced. The burden on cancer patients can be significantly reduced combined with advantages of a robot for endoscopic surgery in thoracic cavity or abdominal cavity. For this purpose, a technique for clarifying cancer tissue stump from serosal side is required. In addition, for example, when taking a capsule endoscope orally, it is necessary to observe a cancer tissue from lumen of digestive tract.

Means for Solving the Problems

The inventors have been developing a rapid intraoperative pathological diagnosis system using cancer cell-specific vital staining and a laser microscope and have found out that cancer cells are stained more densely than normal cells when observing vital-stained cells with a laser microscope after coating certain edible dyes such as curcumin to mucosal surface of digestive tract. The staining allowed rapid detection of cancer cells and further enabled clear visualization of cell morphology including nucleus morphology of cells. As a result, cellular atypia and structural atypia can be reliably distinguished, and a method for detecting and treating micro cancers was successfully developed. In this method, a sterile solution of about 1 mg/mL of an edible dye approved for human ingestion such as curcumin and Red #3 is used and coated to in vivo luminal surface of digestive tract, lymph nodes or ex vivo resection stump, and then allow to stand for about 1~5 minutes. An image can be achieved with a laser microscope within a few seconds. Accordingly, this is a technique that can greatly contribute to rapid intraoperative pathological diagnosis.

Since techniques like a robot for endoscopic surgery in thoracic cavity or abdominal cavity are basically performed from serosal side of an organ, if it is possible to predict the extent of invasion of cancer cells from the serosal side before surgery and determine whether or not cancer cells still remain after surgery, radical resection of cancer will be possible and extirpation extent will be small, and the burden on patients will be greatly reduced.

The present invention provides a method, wherein certain edible dye, such as curcumin, is coated to tissues from luminal surface or serosal side, or by ingestion, the vital-stained tissues or cells near the surgical site are imaged with a laser microscope, and cancer tissues or cancer cells are identified.

That is, the present invention is as follows.

[1] A vital staining test method, characterized by administering a cell stain that enables biological tissue observation with laser irradiation to an organ, and then irradiating the organ with multiphoton laser or confocal laser.

[2] The method according to [1], wherein an organ is irradiated with multiphoton laser or confocal laser from serosal side of the organ.

[3] The method according to [1], wherein an organ is irradiated with multiphoton laser or confocal laser from lumen of the organ.

[4] The method according to any one of [1]~[3], wherein the cell stain is one or more stains selected from the group consisting of sulfuretin, curcumin, Red #3 (erythrosine) and Red #106.

[5] The method according to any one of [1]~[4], wherein the administration of a cell stain is performed by coating, dropping or spraying from serosal side of an organ.

[6] The method according to any one of [1]~[4], wherein the administration of a cell stain is performed by coating, dropping or spraying from lumen of an organ.

[7] The method according to any one of [1]~[4], wherein the administration of a cell stain is oral, intravenous, intraperitoneal, intrathoracic, or intrathecal administration; or subcutaneous, intramuscular, or intra-organ injection.

[8] The method according to any one of [1]~[7], wherein the laser irradiation is performed by using a multiphoton laser microscopic endoscope, a confocal laser microscopic endoscope, or a laser fluorescent microscopic endoscope.

[9] The method for detecting cancer cells, characterized by using the method according to [8] to visualize cancer cells.

[10] The method according to [9] for determining invasion of cancer to regional lymph node tissue when a cancer is present in an organ suspected of having cancer, which comprises administering a cell stain that can enable biological tissue observation with laser irradiation to lymph node tissue using a method of dropping a cell stain from the surface covering the lymph node tissue or injecting a cell stain into the lymph node, and then irradiating the lymph node tissue with multiphoton laser or confocal laser.

[11] The method according to [9], characterized by staining organ tissues with curcumin or sulfuretin in an organs suspected of having cancer, and then laser irradiating the organ tissue from serosal side or lumen using a multiphoton laser microscopic endoscope, confocal laser microscopic endoscope, or laser fluorescent microscopic endoscope, and identifying cell types based on visualized images obtained on cytoplasmic and nuclear morphology of the cells present in the organ tissue.

[12] The method according to [11], which further comprises distinguishing normal cells or tissues from cancer cells or tissues.

[13] The method according to [9], characterized by staining organ tissues with Red #106 in an organs suspected of having cancer, and then laser irradiating the organ tissue from serosal side or lumen using a multiphoton laser microscopic endoscope, confocal laser microscopic endoscope or laser fluorescent microscopic endoscope, comparing the visualized patterns of the capillaries around cancer cells and normal cells in the organ tissues, and detecting the cancer cells based on the disappearance and/or deformation of the capillaries observed around the cancer cells.

[14] The method according to [13], which further comprises distinguishing normal cells or tissues from cancer cells or tissues.

[15] The method according to any one of [1]~[14], which comprises visualizing cell morphology at a depth of 0.05~1.0 mm from organ surface.

[16] The method according to any one of [1]~[15], which further comprises specifying the location of cancer tissue by fluorescently staining the periphery of a cancer tissue in an organ.

[17] The method according to [9], which comprises staining an organ tissue with curcumin or sulfuretin in an organ suspected of having cancer, and then laser irradiating the organ tissue from serosal side or lumen using a multiphoton laser microscopic endoscope, confocal laser microscopic endoscope or laser fluorescent microscopic endoscope, and visualizing Meissner's plexus or Auerbach's plexus present in the organ tissue.

[18] The method according to [17], characterized in that when a primary lesion of a cancer is mucosal epithelium, if the cancer cells have invaded or reached Meissner's plexus, the cancer is judged as an advanced cancer.

[19] The method according to [17], characterized in that when a primary lesion of a cancer is mucosal epithelium, if the cancer cells have invaded or reached the Meissner's plexus and smooth muscle layer, the cancer is judged as an advanced cancer.

[20] The method according to [17], characterized in that when a primary lesion of a cancer is mucosal epithelium, if the cancer cells have not invaded or reached Meissner's plexus, the cancer is judged as an early cancer.

[21] The method according to any one of [9]~[20], which further comprises notifying the detection of cancer cells by sound or light.

[22] The method characterized by using any one of the methods according to [9]~[21] for treating cancer patients by removing cancer cells one by one from serosal side or lumen.

[23] The method characterized by using any one of the methods according to [9]~[21] for confirming cancer cells remaining in a living body from serosal side or lumen after surgery, and removing the cancer cells one by one.

[24] A method for treating colon cancer patients, characterized by using any one of the methods according to [9]~[21].

[25] A method for treating lung cancer patients, characterized by using any one of the methods according to [9]~[21].

[26] A method for treating prostate cancer patients, characterized by using any one of the methods according to [9]~[21].

[27] A method for treating gastric cancer patients, characterized by using any one of the methods according to [9]~[21].

[28] A method for treating esophageal cancer patients, characterized by using any one of the methods according to [9]~[21].

[29] A method for treating bladder cancer patients, characterized by using any one of the methods according to [9]~[21].

[30] A method according to [8] for staining an organ tissue with curcumin or sulfuretin, and then laser irradiating the organ tissue from serosal side or lumen with multiphoton laser microscopy, confocal laser microscopy or laser fluorescence microscopy, and identifying neuronal cell types and neural networks based on visualized images obtained on morphology of cytoplasm and nucleus of neuronal cells present in the organ tissue and nerve fibers, and/or morphology of myelin surrounding the nerve fibers and axons.

[31] The method according to [30], wherein the neuronal cells are autonomic neuronal cells, and the neural networks are Auerbach's plexus and Meissner's plexus.

[32] A method according to [9] for double staining an organ tissue with curcumin, sulfuretin or Red #106, and then laser irradiating the organ tissue from serosal side with multiphoton laser microscopy, confocal laser microscopy or laser fluorescence microscopy, and identifying normal cells or tissues from cancer cells or tissues based on cell images obtained.

[33] A method according to [9] for double staining a tissue of digestive tract with curcumin, sulfuretin or Red #106, and then laser irradiating the organ tissue from serosal side with multiphoton laser microscopy, confocal laser microscopy or laser fluorescence microscopy, and determining the presence or absence of cancer invasion in each layer of the visualized five-layer structure of the digestive tract including epithelial and glandular layers (1), muscularis mucosae (2), submucosal layer (3), muscle layer (4) and serosa (5) based on the differences in images between the structure of normal tissue and structure of cancer cells invasion.

[34] A method characterized by using the method according to [9] for detecting cancer in individuals which comprises a step of identifying that an individual has cancer if the cells are judged to be atypical when comparing with normal cells based on visualized images, or a step of identifying that an individual has cancer if the regularity of distribution pattern of glandular structure and crypt structure is judged to be lost when comparing with normal cells.

[35] A method characterized by using the method according to [17] for diagnosing advanced cancers, which comprises a step in which when a primary lesion of a cancer is mucosal epithelium, the cancer is judged as an advanced cancer based on visualized images if the cancer cells have invaded or reached Meissner's plexus, or a step in which when a primary lesion of a cancer is mucosal epithelium, the cancer is judged as an advanced cancer if the cancer cells have invaded or reached Meissner's plexus and smooth muscle layer.

[36] A method characterized by using the method according to [17] for diagnosing early cancers, which comprises a step in which when a primary lesion of a cancer is mucosal epithelium the cancer is judged as an early cancer based on visualized images if the cancer cells have not invaded or reached Meissner's plexus.

[37] A method for visualizing pancreatic exocrine cells and islets of Langerhan, which uses the method according to [8].

[38] A method for visualizing taste buds present in tongue or soft palate, which uses the method according to [8].

[39] A method for visualizing peripheral nerves such as sciatic nerve, which uses the method according to [8].

[40] A method for visualizing brain tissues, which uses the method according to [8].

[41] A method according to [40], wherein the brain tissues are cerebral cortex, hippocampus, amygdala, hypothalamus or cerebellum.

[42] A method for detecting brain diseases or brain symptoms, which uses the visualized images obtained by the method according to [40] or [41].

[43] A method according to [42], wherein the brain diseases or brain symptoms comprise Alzheimer's disease, cerebral infarction, cerebral hemorrhage, subarachnoid hemorrhage, multiple sclerosis, and spinocerebellar degeneration.

[44] A method for visualizing an ocular tissue, which uses the method according to [8].

[45] A method according to [44], wherein the ocular tissue is retina.

[46] A method for detecting eye diseases or eye symptoms, which uses the visualized images obtained by the method according to [44] or [45].

[47] A method according to [46], wherein the eye diseases or eye symptoms comprise macular degeneration, retinal degeneration, diabetic retinopathy, retinoblastoma, proliferative vitreoretinopathy, glaucoma, retinal detachment and retinal edema.

[48] A method characterized by using the method according to [10] for detecting whether or not cancer cells are present in lymph nodes during a laparoscopic surgery before lymph node resection.

[49] A cancer immunotherapy characterized by destroying only cancer cells one by one that have metastasized to lymph nodes by laser evaporation, recognizing the dead body of cancer cells as immune cells, and attacking cancer cells at primary cancer lesion in activated lymphocytes.

[50] A method for diagnosing any disease that causes an abnormality in location, number, shape, size, or arrangement of cells by visualizing cell structure of digestive tract, cell bodies of neuronal cells in the whole brain and retina, taste and smell sensory cells, endocrine cells, lymph nodes, skeletal muscle, lungs, pancreas, or liver after an oral or intraperitoneal administration of curcumin, and imaging the visualized cell structure with a laser microscope endoscope and fluorescence microscope.

[51] A method characterized by using the method according to [50] for destroying and removing problematic cells one by one by laser irradiation.

[52] A therapy of destroying with laser only undifferentiated cells or cancer cells derived from transplanted iPS cells in regenerative medicine.

[53] A method characterized by using any one of the methods according to [9]~[21] for treating patients with uterine cancer or ovarian cancer.

[54] A method characterized by using any one of the methods according to [9]~[21] for treating patients with breast cancer.

[55] A method characterized by using any one of the methods according to [9]~[21] for treating patients with pancreatic cancer or gallbladder cancer.

[56] A method characterized by using any one of the methods according to [9]~[21] for treating tongue cancer, throat cancer, laryngeal cancer, or thyroid cancer.

[57] A method characterized by using any one of the methods according to [9]~[21] for diagnosing the cause of tonsillitis.

[58] A method according to [57] for diagnoses in cases of leukocytes which invade tonsils, of judging as bacterial infectious tonsillitis if neutrophils invade much, or judging as allergic tonsillitis if eosinophils invade much, or judging as viral infectious tonsillitis if lymphocytes invade much.

[59] A method characterized by using any one of the methods according to [9]~[21] and [38] for analyzing morphology of sensory cells of taste buds and olfactory epithelium to diagnose taste abnormality and/or olfactory abnormality.

[60] A method characterized by using any one of the methods according to [9]~[21] for analyzing skeletal muscle morphology to diagnose lesions of sarcopenia and/or myasthenia gravis.

[61] A method characterized by using any one of the methods according to [9]~[21] for analyzing morphology of endocrine cells of pancreatic islets of Langerhans and/or thyroid to diagnose diabetes and/or Basedow's disease.

Effects of the Invention

State of cells in a tissue and a tissue can be confirmed from serosal side according to the present invention.

According to the method of the present invention, an edible dye approved for human ingestion, such as sulfuretin, curcumin, Red #3, or Red #106 solution, is sprayed from luminal or serosal tissue and allow to stand for about 1~5 minutes, or ingesting a solution of curcumin. Cell morphology can be imaged and identified from the serosal side with a multiphoton laser microscope or a confocal laser microscope. Curcumin and Red #3 can stain cells that overexpress STAT3 and RAS, which are cancer-related gene products respectively. When the dye is sprayed according to the method, it takes less than 5 minutes to achieve images. A surgeon can search a plurality of tissue sites of interest continuously. That is, the present invention provides a method for identifying tissues and cells necessary for a surgeon to make an immediate pathological diagnosis during surgery. The images from a multiphoton laser microscope or a confocal laser microscope obtained by the method are very clear. The nuclear morphology of individual cells is clearly visualized. Accordingly, cellular atypia and structural atypia of cancers can be determined reliably.

BRIEF DESCRIPTION OF THE FIGURES

FIG. 5G is a diagram visualizing glandular structure and crypt structure of an isolated large intestine of a mouse (normal mucosal tissue) by vital staining with Red #106 and imaging from serosal side with a multiphoton laser microscope.

FIG. 6B is a photograph taken by focusing on epithelial and glandular layers (1) and muscularis mucosae (2) (see FIG. 5a). As indicated by the figures, glands are stained by curcumin. Connective tissues and capillaries are stained by Red #106. Furthermore, smooth muscle (muscularis mucosae) is stained by curcumin.

FIG. 13 shows photographs taken with a confocal laser microscope inserted into a mouse chest after incising the mouse chest, and staining normal lung tissue with curcumin (A) or Red #106 (B) from the surface of pleural side. As indicated by the photographs, the structure of alveolar can be clearly observed.

FIG. 22 is a diagram showing, at high magnification, an example of visualization with a laser microscope of sensory neuronal cells of a taste bud, which is a taste sensory device, after vital staining by coating curcumin onto tongue mucosa.

FIG. 25 is a diagram showing, at high magnification, an example of visualization with a laser microscope of olfactory nerve fibers after vital staining by intraperitoneal administration of curcumin. As indicated by the figure, curcumin can stain myelin sheath.

FIG. 26 is a diagram showing, at high magnification, examples of visualization with a laser microscope of olfactory receptor neurons, which are odor sensory cells, after vital staining by coating curcumin onto nasal mucosa.

FIG. 27 is a diagram showing, at high magnification, an example of visualization with a laser microscope of thyroid after vital staining by intraperitoneal administration of curcumin. Furthermore, the figure shows a hematoxylin eosin (HE) staining image of thyroid tissue.

FIG. 28 is a diagram showing, at high magnification, examples of visualization with a laser microscope of actin/myosin striations, nuclei and myofibers of skeletal muscle after vital staining by coating curcumin onto fascia.

FIG. 29 is a diagram showing, at high magnification, examples of visualization with a laser microscope of structure of bright center and dark shell of secondary nodule of lymph node after vital staining by coating curcumin onto lymph node.

EMBODIMENTS FOR CARRYING OUT THE INVENTION

Figure 1:
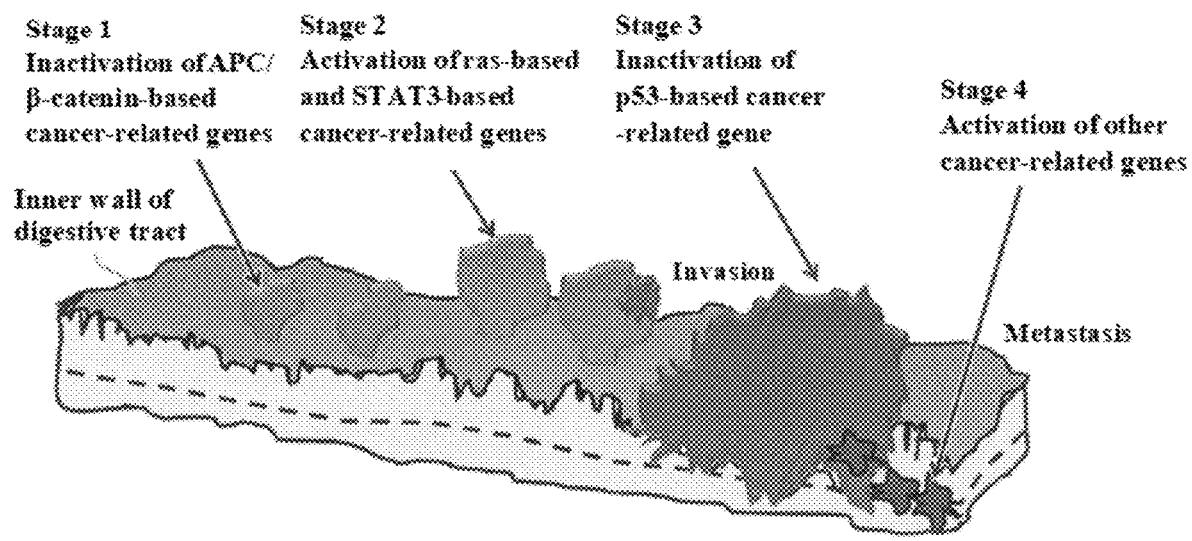
FIG. 1 is a schematic diagram showing stepwise mutation and activation of an oncogenic gene of a living cell group on inner wall of digestive tract, and process of cancer development, invasion and metastasis.

Next, embodiments of the present invention will be described with reference to the figures. However, the technical scope of the present invention is not limited by these embodiments. The present invention can be implemented in various forms without changing its abstract.

Examples of the cell stains used in the present invention include vital stains consisting of one or more edible dye compounds. The dye compounds are selected from the group of fluorescent dyes including tar dyes (Red #3 (erythrosine), Red #104 (phloxine), Red #105, Red #106, Green #3 (Fast Green FCF), Red #2, Red #102, Blue #2 (indigo carmine), Yellow #4 (tartrazine), Yellow #5 (Sunset Yellow FCF), etc.), iridoid dyes (Haimeron P-2 (Gardenia Blue: geniposide), HI BLUE AT (Gardenia Blue dye: geniposide), etc.), carotenoid-based dyes (Haimeron P-2 (yellow dye: crocin), annatto (annatto N2R25, achiote fruit: bixin, norbixin), Haimeron P-2 (Gardenia Blue: geniposide), crocin G150 (Gardenia Yellow dye), crocin L (Gardenia Yellow dye), β-carotene, annatto WA-20 (annatto dyes, achiote seeds: norbixin), etc.), flavonoid-based dyes (HI RED G150 (grape peel dye, anthocyanin), HI RED RA200 (red radish dye: pelargonidin acyl glucoside), HI RED V80 (purple potato dye: cyanidin acyl glucoside and peonidin acyl glucoside), apigeninidine (kaoliang dye), cyanidin, delphinidin (eggplant dye), fisetinidine (*Acacia mearnsii* dye), malvidin (blue sweet pea dye), pelargonidin, robinetinidine (*Robinia pseudocacia* tree pigment), tricetinidine (black tea dye), petunidin (red berry dye), capsanthin (capsicum dye), epigallocatechin gallate, green tea, Safflower Y1500 (safflower dye, safflomin A+B), curcumin, sulfuretin, myricetin (grape, onion dye), or quercetin (onions, citrus dyes)), quinoid-based dyes (cochineal (Cochineal Red AL, carminic acid), HI REDS (lac dye/laccaic acid), etc.), betalain-based dyes (HI RED BL (red beet dye: betanin, isobetanin), etc.), indocyanine green and gingerol (ginger spicy ingredient).

Preferred examples of the cell stains used in the present invention include one or more stains selected from the group consisting of sulfuretin, curcumin, Red #3 (erythrosine) and Red #106.

There are no particular restriction on the method of administering the cell stains, and for example, a cell stain of the present invention may be administered directly into the lumen of an organ or administered submucosally, or may be administered from serosal side of an organ. As these administration methods, administration by coating, dropping or spraying can be applied. Furthermore, as an administration method of a cell stain, oral, intravenous, intraperitoneal, intrathoracic, or intrathecal administration can also be used. The administration method can be selected depending on the organ or site of the organ to be stained. When the stain has weak stainability, the mucosal surface is treated with pronase to remove the mucus, thereby improving the visibility of cell structure. When the stain is to be applied directly to the inner surface of a lumen (for example, by coating or spraying), the dosage form is preferably liquid, although forms such as granules, tablets, or the like may also be used. Besides, appropriate added components, for example, additives such as isotonizing agents, pH regulators, stabilizers, thickening agents, antiseptic agents, aromatics or adhesives may be combined with the stains depending on the dosage form and other factors. For example, pronase may be preadded to the stains of the present invention.

FIG. 1 is a schematic diagram showing a stepwise process of malignant transformation of a living cell group on the surface of inner wall of digestive tract. In FIG. 1, the process of malignant transformation of a living cell group is shown in order of stages 1, 2, 3 and 4.

The stage 1 is a stage where malignant transformation starts in part of a living cell group. It is considered that stage 1 occurs when activity of APC/β-catenin-based cancer-related gene is weakened and the function of suppressing cell proliferation is reduced. At this stage, the proliferation of cells is slightly enhanced, indicating that at least a precancerous state that the cells can become cancer cells in the future is expressed.

The stage 2 is a precancerous state in which a cancer has progressed more than stage 1. It is considered that the activity of ras-based cancer-related gene is enhanced and cell proliferation is enhanced in stage 2. It is also considered that STAT3-based cancer-related genes may be activated at this stage. The size of a cancer cell population is small, and its diameter is, for example, 0.1~0.4 mm. The diameter of a cancer cell population is a diameter of a circle having the same area as the area of the cancer cell population when the cancer cell population is regarded as a circle. Life of a patient is not immediately threatened in this stage. However, it is desirable to make a treatment plan for the future.

The stage 3 is a stage in which part of a living cell group is in an invading state, where cancer cells are revealed. It is considered that stage 3 occurs when the activity of p53-based cancer-related genes is weakened and the function of suppressing cell proliferation is reduced. In this stage, the activities of both p53-based and APC/β-catenin-based tumor suppressor gene products are weakened, and the function of suppressing cell proliferation is greatly reduced. Therefore, the proliferation of cancer cells accelerates, and the cancer cells invade surrounding tissues. By proceeding to stage 3, the diameter of a cancer cell population reaches 0.5 mm or more, and if left as it is, the cancer that induces death of an individual is completed.

The stage 4 is a stage in which cancer cells completed in stage 3 have become cancerous, further cause genetic mutations, and have progressed to malignant cancers that are susceptible to cell proliferation, invasion and metastasis. This stage is when cancer metastasis to other distant organs other than digestive tract begins, which is a life-threatening and dangerous stage. It is considered that the progress speed from stage 1 to stage 4 depends on the activation state of the cancer-related gene.

Figure 2:
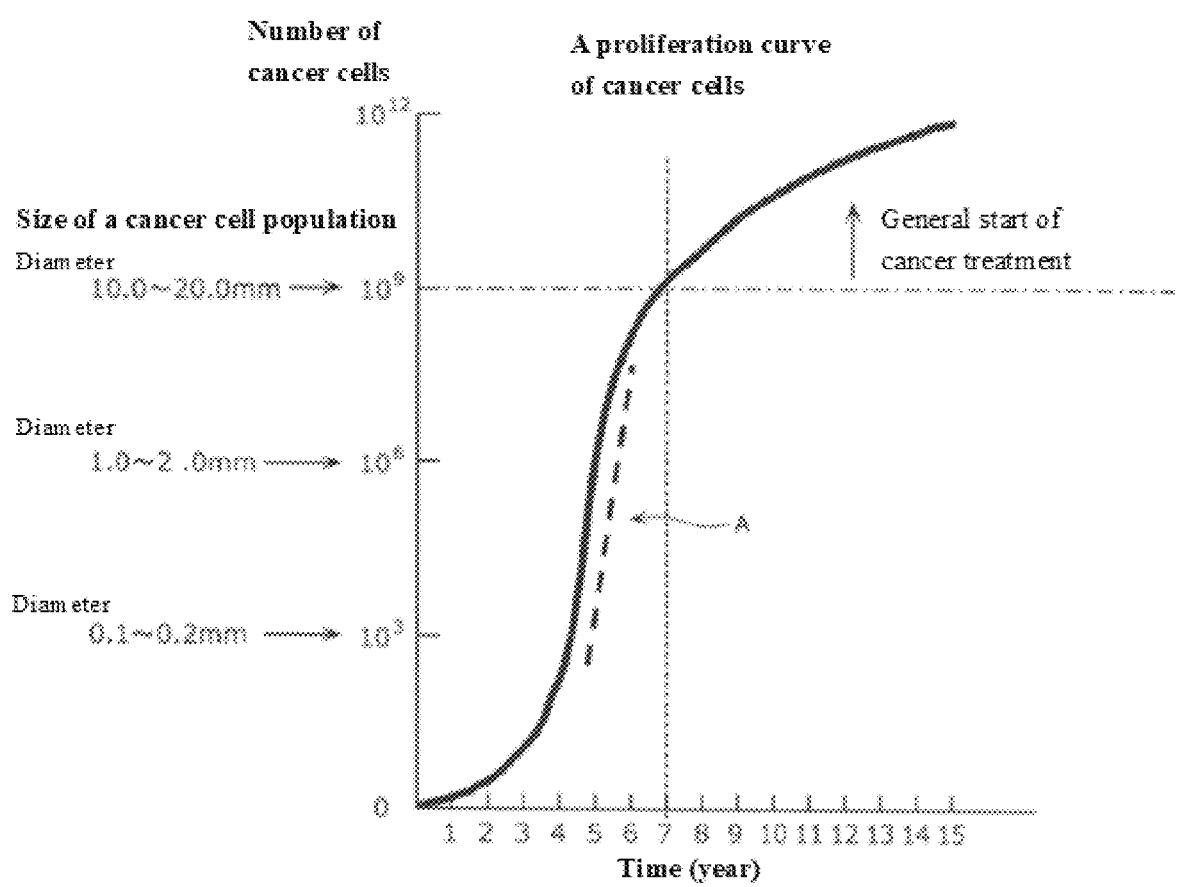
FIG. 2 is a diagram showing an example of a proliferation curve of human cancer cells.

FIG. 2 is a diagram showing an example of a proliferation curve of human cancer cells. As shown in FIG. 2, generally, the number of cancer cells increases according to a predetermined proliferation curve. For example, the slope of the proliferation curve is small during the first 3 years when malignant transformation is about to begin (a period when the diameter of a cancer cell population is less than 0.2 mm), but turns large after 4 years (a period when the diameter of a cancer cell population is 0.5 mm or more), and decreases slightly after 7.5 years. Generally, a cancer is detected clinically and a treated after 7 years. This is because a cancer cell population cannot be detected unless its diameter reaches 10 mm or more. Currently, a cancer is generally found after its diameter exceeds 20 mm. Therefore, it is normally treated by removal of cancer cells by surgical resection.

It should be noted in FIG. 2 that the size of a cancer cell population increases exponentially in the extent indicated by the dashed line A in the proliferation curve of FIG. 2. This exponential increase indicates that cancer cells in a cancer cell population have completed gene mutation in stages 1~3 of cancer which should occur, and cancer cells are dividing repeatedly at a constant and uniform rate. In the early stages of this exponential increase, that is, when the cancer-related gene expression pattern is abnormal, but the cancer cell population itself is as small as 1 mm or less in diameter. If these cancer cell populations (very early cancer) can be detected, the cancer can be cured radically since these very early cancers are small enough to be completely and easily removed. In this way, at the very early stage, if the malignancy of malignant transformation can be captured as an abnormality in the expression pattern of cancer-related genes, cancer can be treated radically before reaching dangerous stage.

In order to detect very early cancer, the inventors have tried to determine malignancy of malignant transformation by imaging cancer-related gene expression pattern of a living cell group with a multiphoton laser microscope or a confocal laser microscope, and visualizing the activation state of cancer-related genes.

For the visualization of expression patterns of cancer-related genes in living cells, The inventors stained a cancer-related gene product with a chromatic color using a stain containing an edible dye and performed imaging. An edible dye is a kind of natural dye or artificial dye that is permitted to be administered to human being (For example, a dye for food coloring, or a dye that can be taken in supplements).

Specifically, a stain containing curcumins ($C_{21}H_{20}O_6$) can be used to selectively stain a STAT3-based cancer-related gene product. In addition, a stain containing Red #3 (erythrosine) can be used to selectively stain the expression pattern of ras-based cancer-related gene.

More specifically, as a stain containing curcumins, a solution containing 1% by weight of curcumin was prepared. As a stain containing Red #3, a solution containing 1% by weight of phloxine was prepared. As a stain containing curcumins, a curcumin solution (for example, a stock solution is 5% curcumin solution containing 45% glycerol and 50% ethanol.) diluted with physiological saline to 1/5~1/100 can be used. As a stain containing 1% Red #3, a phloxine solution at the concentration ranging from 10 mg/mL (its stock solution) to 1/10 diluted one can be used.

(i) Chemically synthesized curcumin is diluted to about 1 mg/ml in a solution containing 0.45% of glycerin and 0.5% of ethanol. The solution obtained is used.

(ii) 1 g of Okinawa curcumin powder is dissolved in 10 ml of PBS and diluted to about 1 mg/ml. The solution obtained is used.

Both (i) and (ii) are sterilized with sterilizing filters immediately before being administered to a living body.

When a stain containing curcumins is used, the expression of a STAT3-based cancer-related gene product in living cells can be visualized by staining. In addition, when a stain containing Red #3 is used, the expression of ras-based cancer-related genes in living cells can be visualized by staining. After the staining, excess stain can be removed by rising. Excess staining solution can be removed by performing rising 3 times for about 10 seconds each time with a physiological solution such as physiological saline or phosphate buffered saline that does not damage cells or living tissue. When double staining using different stains, it becomes possible to simultaneously analyze the expression levels of STAT3-based and ras-based cancer-related gene products. The staining time of each stain can be 1~5 minutes. At the above-mentioned concentration, if it is within 10 minutes from the start of staining, it does not penetrate into the nucleus in a cell, even if it penetrates into cytoplasm. Accordingly, it is possible to clearly visualize the nucleus surrounded by the cytoplasm, which makes analysis clearer.

The staining times until observation are 1~30 minutes after administration by coating directly to mucosal or organ surface, 30 minutes~1 hour after oral administration, 3 minutes~1 hour after intravenous administration, 3 minutes~1 hour after intraperitoneal administration, 3 minutes~1 hour after administration by subcutaneous injection, 3 minutes~1 hour after administration by intramuscular injection, 5~30 minutes after administration by intra-organ injection, or 3 minutes~1 hour after intrathoracic or intrathecal administration.

The staining of cancer cells with the above-mentioned cell stains can be performed directly on organs. Organs derived from human being or animals can be used. The organ to be stained may be an extirpated organ or an in-vivo organ. Examples of organs include, but are not limited to, large intestine, lung, prostate, stomach, esophagus, bladder, lymph nodes, and the like. In the case of staining a lymph node, it is preferable to apply a staining solution after exfoliating the surface tissue covering a lymph node tissue in order to increase the permeability of a staining solution. Cells stained with a cell stain can be imaged using a multiphoton laser microscope or a confocal laser microscope. When multiphoton laser is used, the wavelength of laser is preferably in the extent of 600~1600 nm in order to achieve a sufficient imaging depth and resolution from an organ surface. When confocal laser is used, the wavelength of laser is preferably in the extent of 400~700 nm.

The application of a staining solution to an organ can be performed from serosal side covering the organ surface. For tubular organs such as large intestine, stomach, and esophagus, it can also be performed from lumen side. Applying means coating, dropping or spraying a cell staining solution onto an organ. For the purpose of pathological diagnosis of an organ resected after an operation, if a removed organ is tubular, tissue staining can be performed from luminal side. However, in order to identify a resection site or a cancer invasion site during surgery, it is desirable to perform tissue staining from serosal side of an organ. This is because, for example, robot technology for endoscopic surgery on the abdominal cavity or the like basically performs an operation from serosal side of an organ, and thus it requires tissue staining on the serosal side. When a staining solution is applied from serosal side, a sterilized staining solution is coated, dropped or sprayed to an organ serosa in the surgical field, and within 10 minutes after the application of the staining solution, preferably 1~5 minutes, and more preferably 1~3 minutes, the organ is rinsed with physiological saline or the like, and the staining solution is removed. Immediately thereafter, stained images can be observed with a multiphoton laser microscope or a confocal laser microscope. In addition, a stain can be administered to the whole body before an operation, and a tissue can be observed with a laser microscope during the operation. As administration methods, oral administration or intravenous administration can be used.

Regarding staining an organ tissue, the object in the organ to be visualized differs depending on the stain used. For example, curcumin and Red #3 are suitable for staining epithelial and glandular cells, as well as cancerous cells derived from them. On the other hand, Red #106 is suitable for staining connective tissues and capillaries. By laser irradiation, curcumin gives a green fluorescent color, while Red #3 and Red #106 give a red fluorescent color. Therefore, double staining with curcumin and Red #106 makes it easier to identify structure of tissue cells by superimposing stained images. As a result, detection of fine cancer tissue with diameter of about 1 mm and invasive cancer cell populations can be detected.

Figure 4:
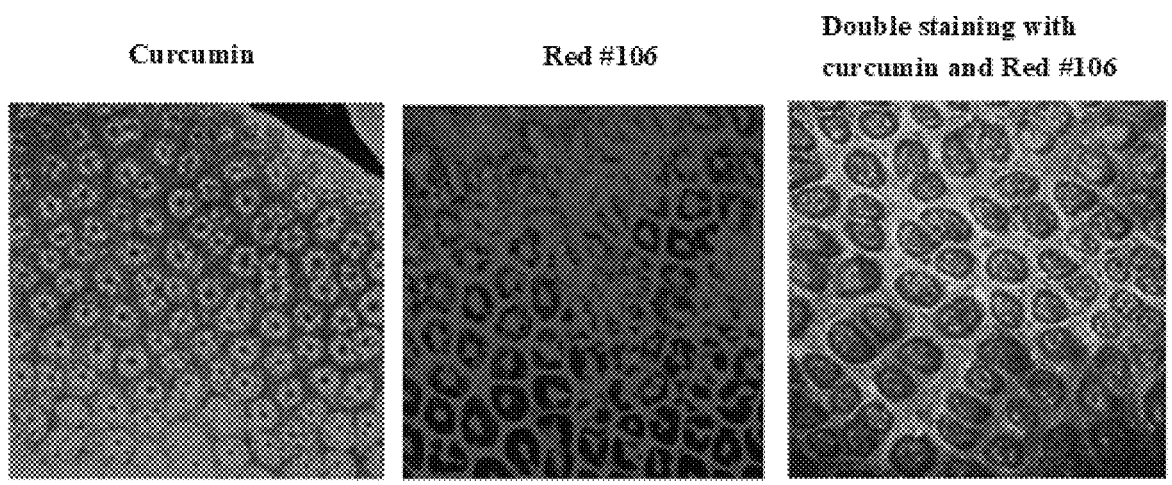
FIG. 4 shows photographs taken with a multiphoton laser microscope from lumen side from an isolated large intestine of a mouse (normal mucosal tissue) vital-stained with curcumin and Red #106 from the lumen side.

FIG. 4 shows isolated large intestine of a mouse (normal mucosal tissue) vital-stained with curcumin and Red #106 from lumen side and photographed with a multiphoton laser microscope from the lumen side. As a result, curcumin stains cytoplasm of epithelial and glandular cells, and Red #106 stains connective tissue, capillaries and cell membranes of epithelial and glandular cells. Accordingly, it is indicated that structures of tissue cells can be clearly identified by double staining.

Figure 3A:
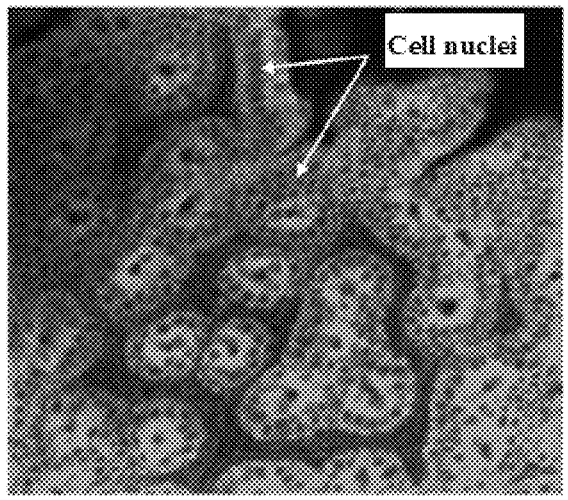
FIG. 3A-B show photographs taken with a multiphoton laser microscope from lumen side of an isolated large intestine of a mouse (normal mucosal tissue and cancer tumor site) stained with curcumin from the lumen side, wherein (A) is a photograph of normal mucosa of large intestine and (B) is a photograph of a tumor site of colon cancer.
Figure 3B:
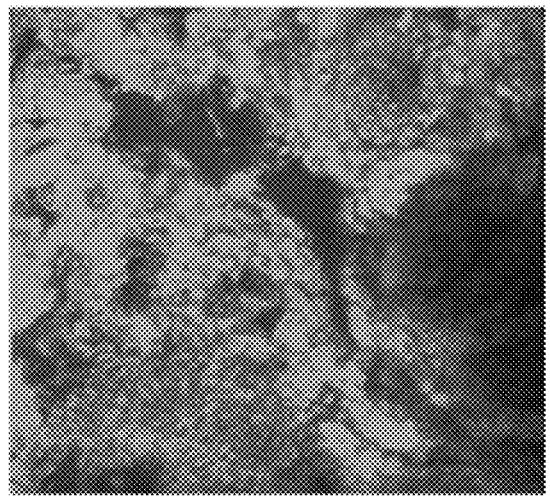

It was found out by tissue staining that laser microscope observation images of normal tissue without cancer cells and those of tumor tissue with cancer cells are different. For example, when mucosa of large intestine is stained with curcumin (see FIG. 3), in normal mucosal tissues of large intestine, the cytoplasm of epithelial cells and gland cells is stained, but the nucleus is not stained. Thus, morphology of individual cells and nuclei is clearly visible. On the other hand, in the tissue of a tumor site of colon cancer, the size of each cell is uneven. The nucleus is large. The arrangement or sequence of the cells is uneven. Further, dissociation of cell adhesion is observed, which is judged to be cellular atypia. Moreover, in cancer tissues, cell populations are not aligned and arranged on basement membrane and do not form glandular structures, which is judged to be structural atypia. According to the method of the present invention, cancer cells can be detected, that is, pathological diagnosis of cancers can be performed based on images which indicate the differences between normal tissues and cancer tissues as described above.

Figure 5A:
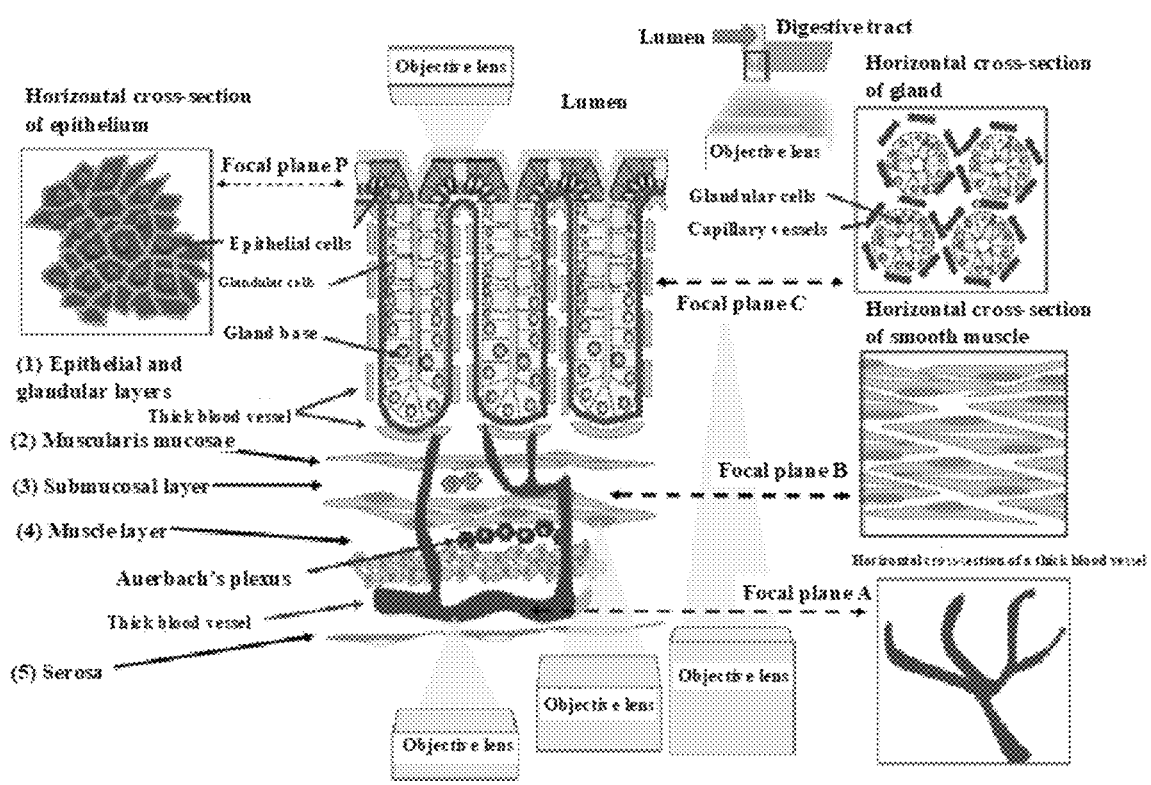
FIG. 5A is a diagram illustrating tissue structure of a normal large intestine, which shows epithelial and glandular layers (1), muscularis mucosae (2), submucosal layer (3), muscle layer (4) and serosa (5) in the order from the surface facing the lumen through which food passes towards deep parts.

Further, invasion of cancer cells can be detected in relation to five-layer structure of normal large intestine. The tissue structure of normal large intestine is shown in FIG. 5a, and the five-layer structure is shown as (1) to (5). When imaging with a confocal laser or a multiphoton laser microscopic endoscope, normal large intestine consists of five layers, which are epithelial and glandular layers (1), muscularis mucosae (2), submucosal layer (3), muscle layer (4) and serosa (5) in the order from the surface facing lumen through which food passes towards deep parts.

The surface facing the lumen is covered all over by the epithelial and glandular layers (1). The epithelial cells form glandular structures that are vertically depressed from the surface in an octopus shape (The vertically depressed structures are also called crypt structures.) at certain intervals. The epithelium looks like a sheet of cells in which epithelial cells are tightly aggregated, as shown by focal plane P in FIG. 5a. On the other hand, as shown by focal plane C in FIG. 5a, the glandular structure is in a shape in which about 10 gland cells are arranged concentrically toward the central aperture, and capillaries having a diameter of about 10 μm are surrounded around the outside thereof. The height of gland is about 0.5~1.0 mm, and its part at one third of the depth is called gland base. The cells in this part divide and renew gland cells and epithelial cells. It is considered that a cancer is caused by abnormally enhanced division of cells at the gland base. The muscularis mucosae (2) is a layer of thin smooth muscle present deep in the glandular structure. When a cancer has not developed beyond the muscularis mucosae, it is called an early stage cancer. The submucosal layer (3) is a layer of loose connective tissue. The muscle layer (4) is a layer of thick smooth muscle that governs intestinal peristalsis. (As shown by focal plane B, it has been found out that this layer contains a population of elongated smooth muscle cells.) Inside this smooth muscle layer, a network of autonomic nerves controlling the movement of this smooth muscle is distributed, which is called Auerbach's plexus. Furthermore, inside the muscle layer, there are also thick blood vessels that supply blood to capillaries around epithelia and glands. (As shown by focal plane A, thick blood vessels with a diameter of 20 μm or more are observed in this layer.) The serosa (5) is a layer consisting of flat cells.

In the above five-layer structure, curcumin was found to stain glandular cells in epithelial and glandular layers (1) severely positive, the smooth muscle in muscularis mucosae (2) severely positive, the smooth muscle in muscle layer (4) mildly positive, and Auerbach's plexus inside muscle layer severely positive, while Red #106 was found to stain a network of capillaries surrounding the glandular structures of epithelial and glandular layers (1) severely positive, the smooth muscle in muscularis mucosae (2) mildly positive, the smooth muscle in muscle layer (4) mildly positive, and the wall of a thick blood vessel inside muscle layer severely positive. Visualization of the five-layer structure of normal large intestine and major cell structures by these vital stains is a very useful clue in determining the extent of cancer invasion. That is, whether or not there is a cancer invasion can be determined accurately by combinations of the finding that the above normal structure does not exist at a normal position with a normal distribution pattern (disappearance of the regular distribution of crypt structures at the gland base by Red #106 at the cancer site, FIG. 12) and the finding that there are cells that should not be present in places where they should not be present in normal cases (many large cells positive for curcumin staining are chronically scattered inside smooth muscle layer. See FIG. 10A and FIG. 10B).

Since it just takes a short time to perform the procedures from staining of organ tissue to observing with a laser microscope, pathological diagnosis of cancer can be applied to pathological diagnosis in-vivo during surgery. In general, pathological diagnosis of cancer is performed based on the difference in size and shape of cells (cellular atypia) and the disorder in structure of tissues (structural atypia). Those with severe atypia are considered to be cancer (malignant), and those with mild atypia are considered to be benign.

Figure 5B:
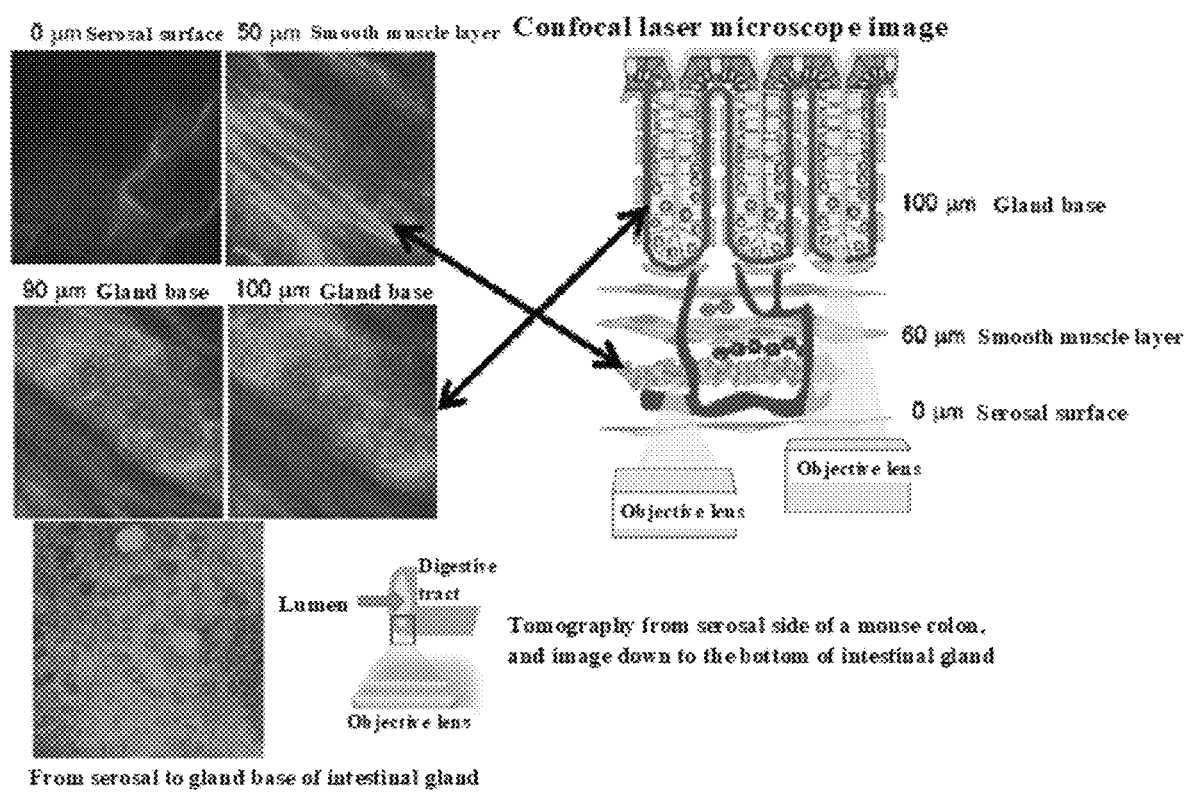
FIG. 5B shows photographs taken with a multiphoton laser microscope from serosal side while changing focal length from an isolated large intestine of a mouse (normal mucosal tissue) stained with curcumin from lumen side. The numbers above the photographs indicate focal length from the serosal side.

In tissue observation with a laser microscope, the focal plane with respect to an organ can be changed by manipulating the position of objective lens of the laser microscope. By this operation, cell morphology from an organ surface to a depth of 0.05~1.0 mm can be clearly observed as tomographic images. For example, in case of observing the tissue of large intestine from serosa side, when the depth of focus is changed sequentially from serosa toward lumen, relatively thick blood vessels which are close to the serosa, the smooth muscle layer, the Auerbach's plexus which is located inside and controls the movement of smooth muscle, and then the glandular structure including capillaries can be observed. By observing a smooth muscle layer, even cancer cells that have invaded into smooth muscle layer can be detected. FIG. 5b shows the results of staining an isolated large intestine (normal mucosal tissue) of a mouse with curcumin from luminal side and photographing with a multiphoton laser microscope while changing the focal length from the serosal side. In the tissue structure of large intestine described above, the surface of serosa (5) can be observed clearly at the focal length of 0 μm; the smooth muscle of muscle layer (4) can be observed clearly at the focal length of about 50 μm, and the glandular structure (crypt structure) of epithelial and glandular layers (1) can be observed clearly at a focal length of 80~160 μm.

Figure 5C:
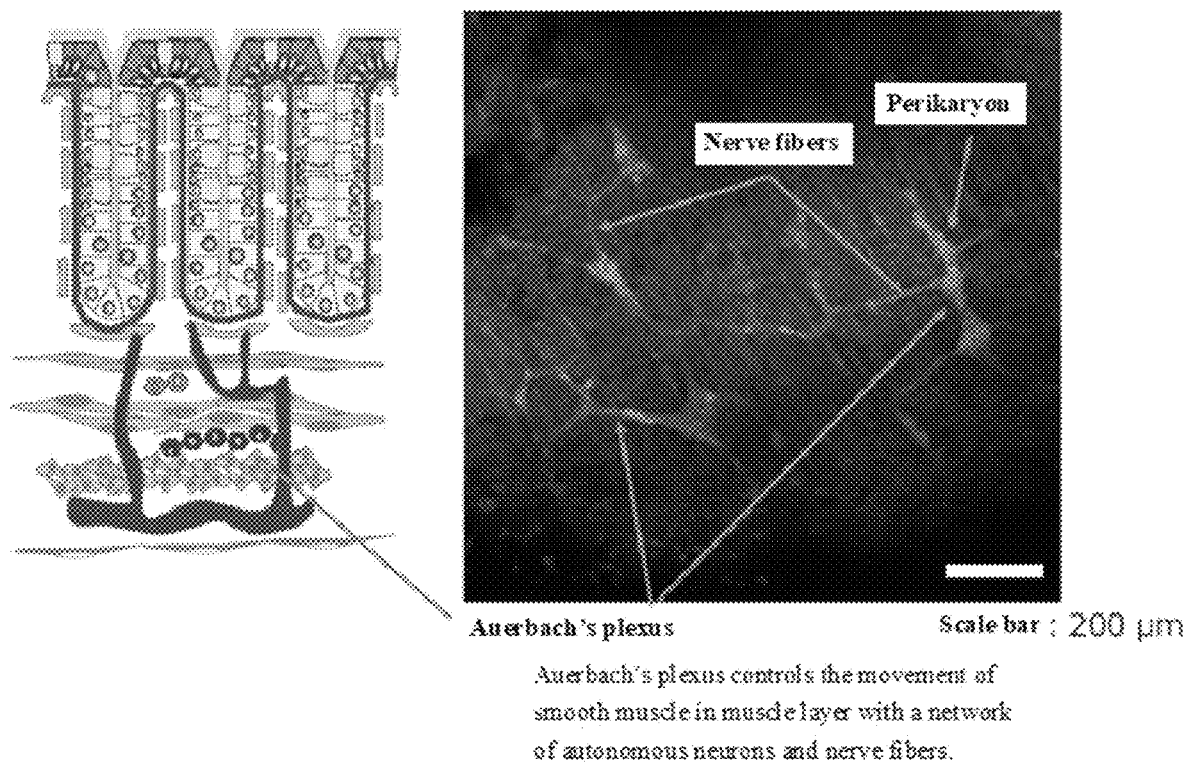
FIG. 5C is an image, at low magnification, taken with a confocal laser microscope of Auerbach's plexus in positively stained muscle layer by vital staining an isolated large intestine of a mouse (normal mucosal tissue) with curcumin from serosa side. This photograph is taken by focusing on muscle layer (4) (see FIG. 5A).

In an embodiment, plexus can be visualized by using the method of the present invention. FIG. 5c is an image obtained by vital staining an isolated large intestine (normal mucosal tissue) of a mouse to from serosa side with curcumin and observing it with a confocal laser microscope. As indicated by the figure, Auerbach's plexus in muscle layer is stained positively. That is, it is understood that curcumin visualizes Auerbach's plexus as a network-like structure because it stains perikaryon darkly, while stains nerve fibers lightly. The Auerbach's plexus belongs to autonomic nervous system and consists of perikaryon and nerve fibers that connect them.

Figure 5D:
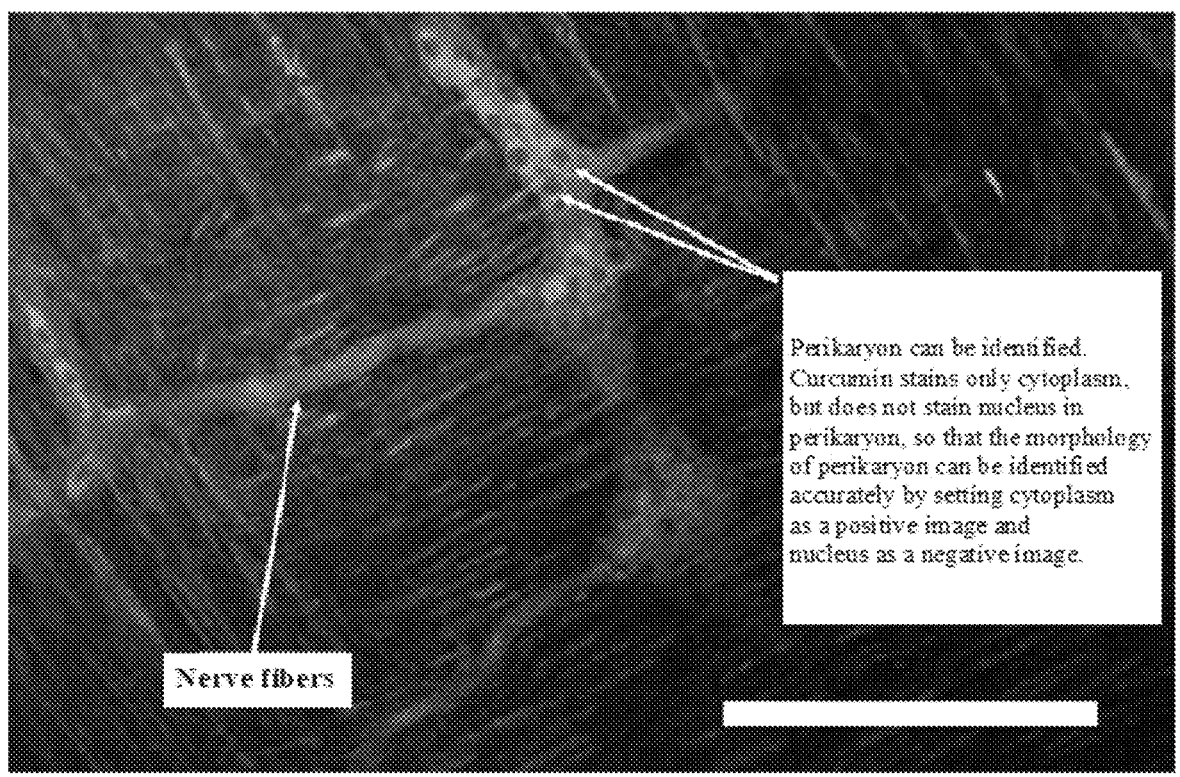
FIG. 5D shows, at high magnification, an example of visualization with a confocal laser microscope of Auerbach's plexus in vital-stained muscle layer with curcumin from serosa side in an isolated large intestine of a mouse (normal mucosal tissue), and that perikaryon can be identified.

FIG. 5d shows an image, at high magnification, of the above-mentioned Auerbach's plexus in muscle layer observed with a confocal laser microscope. As indicated by the figure, perikaryon can also be identified. Regarding the perikaryon, curcumin stains only the cytoplasm and does not stain the nucleus, so that cytoplasm is recognized as a positive image and nucleus is recognized as a negative image. Thereby, the morphology of perikaryon can be accurately determined. Cancer cells develop in epithelial and glandular layers (1) (see FIG. 5a), then spread to other layers, and migrate. (This phenomenon is called cancer cell invasion.) It is known that invading cancer cells tend to move along blood vessels and peripheral nerves. However, the ability to visualize Auerbach's plexus in muscle layer by vital staining with curcumin results in visualization of cancer invasion pathways, which is useful in determining the extent of cancer invasion.

Figure 5E:
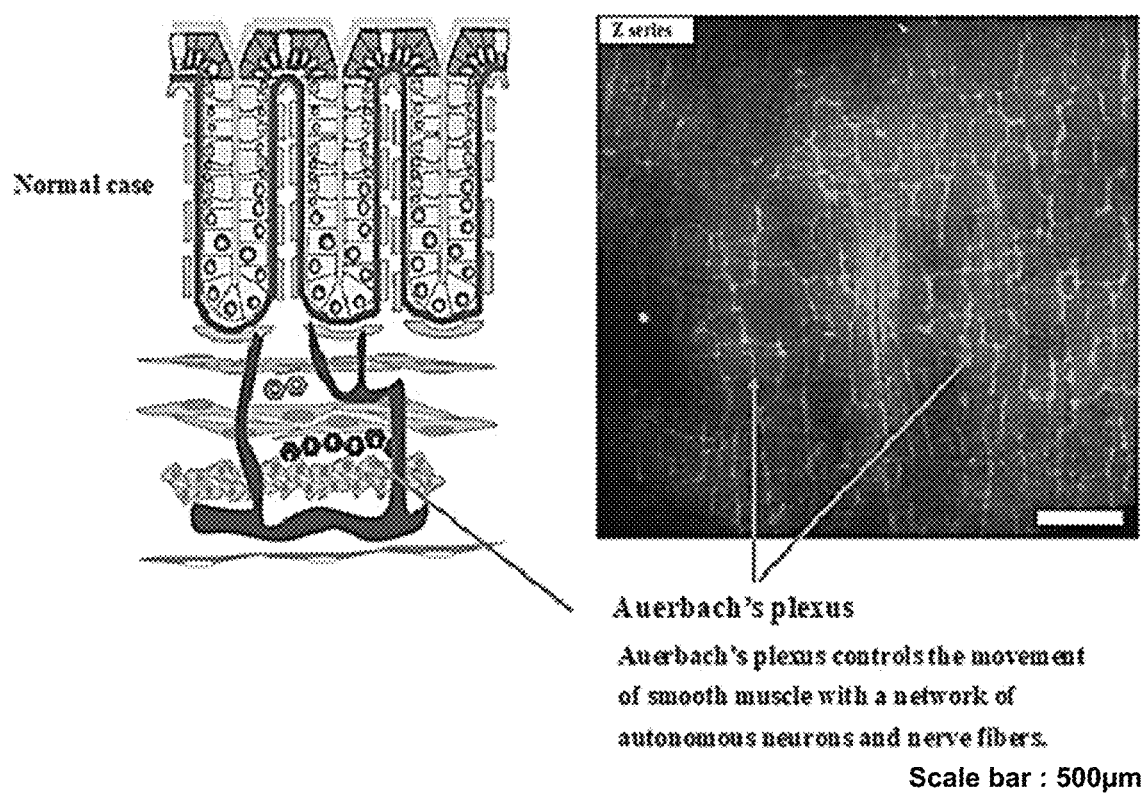
FIG. 5E shows an image taken with a multiphoton laser microscope of Auerbach's plexus in muscle layer in an isolated large intestine of a mouse (normal mucosal tissue) visualized by vital staining with curcumin from serosa side.
Figure 5F:
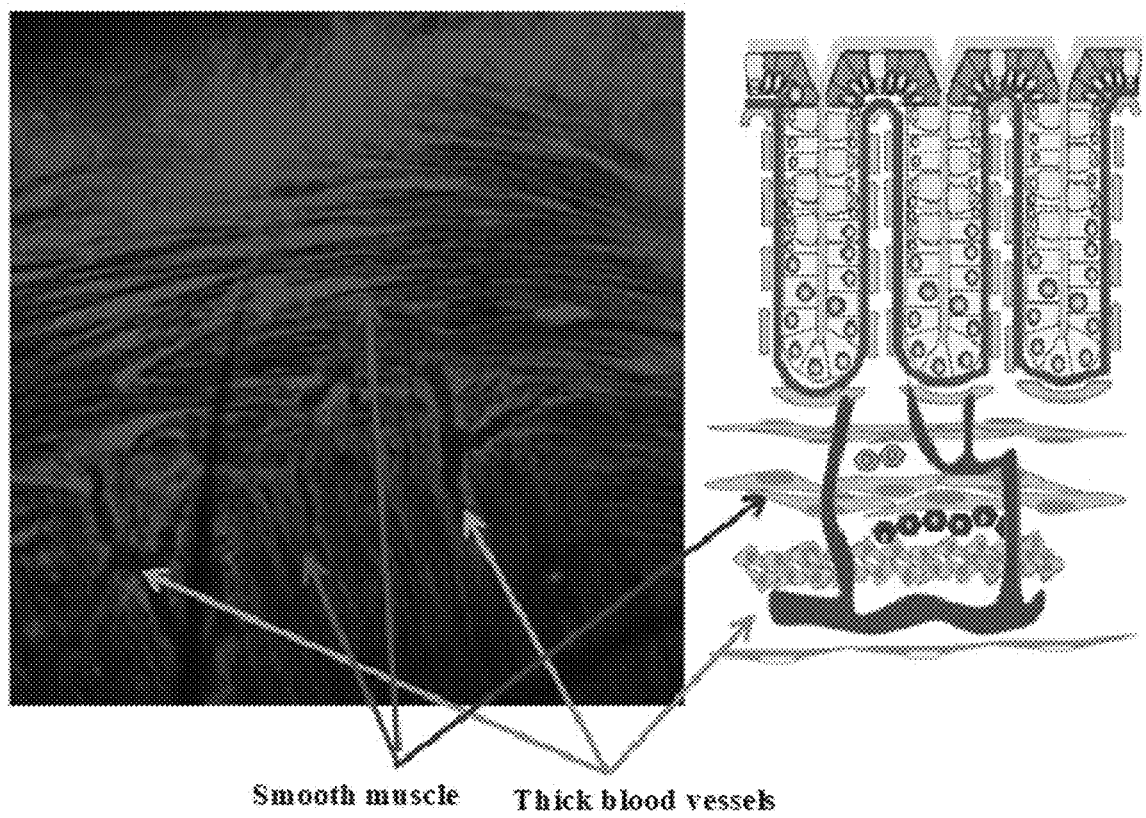
FIG. 5F is a diagram visualizing thick blood vessels and smooth muscle of an isolated large intestine of a mouse (normal mucosal tissue) by vital staining with Red #106 and imaging from serosal side with a multiphoton laser microscope. This photograph was taken by focusing on muscle layer (4) (see FIG. 5A), and it shows that smooth muscle and blood vessel wall are stained by Red #106.
Figure 6A:
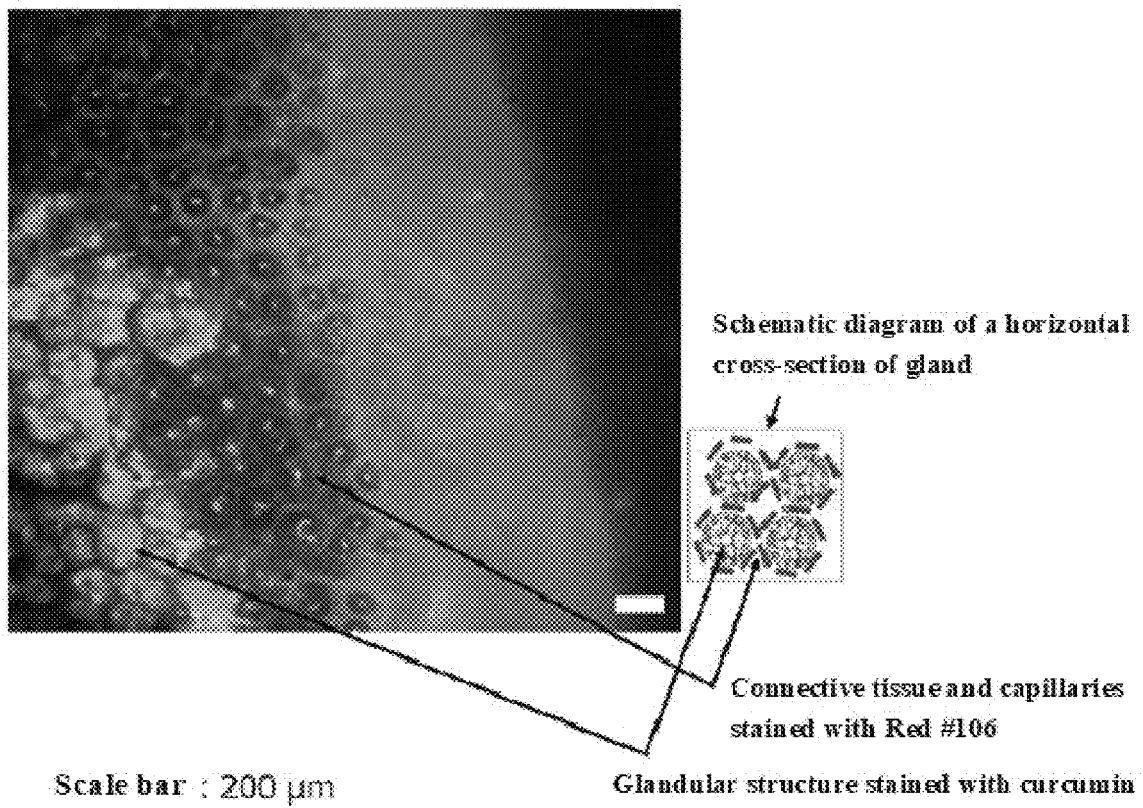
FIG. 6A and FIG. 6B show photographs taken with a confocal laser microscope from serosal side by focusing on epithelial and glandular layers (1) (see FIG. 5a) after incising the abdomen of a mouse and double staining the tissue of large intestine with curcumin and Red #106 from serosal side of the large intestine (normal tissue). As indicated by FIG. 6A, curcumin positively stains gland cells, so that glandular structure is visualized. Red #106 positively stains connective tissue and capillaries as circumferential structures, so that crypt structure can be identified.
Figure 6B:
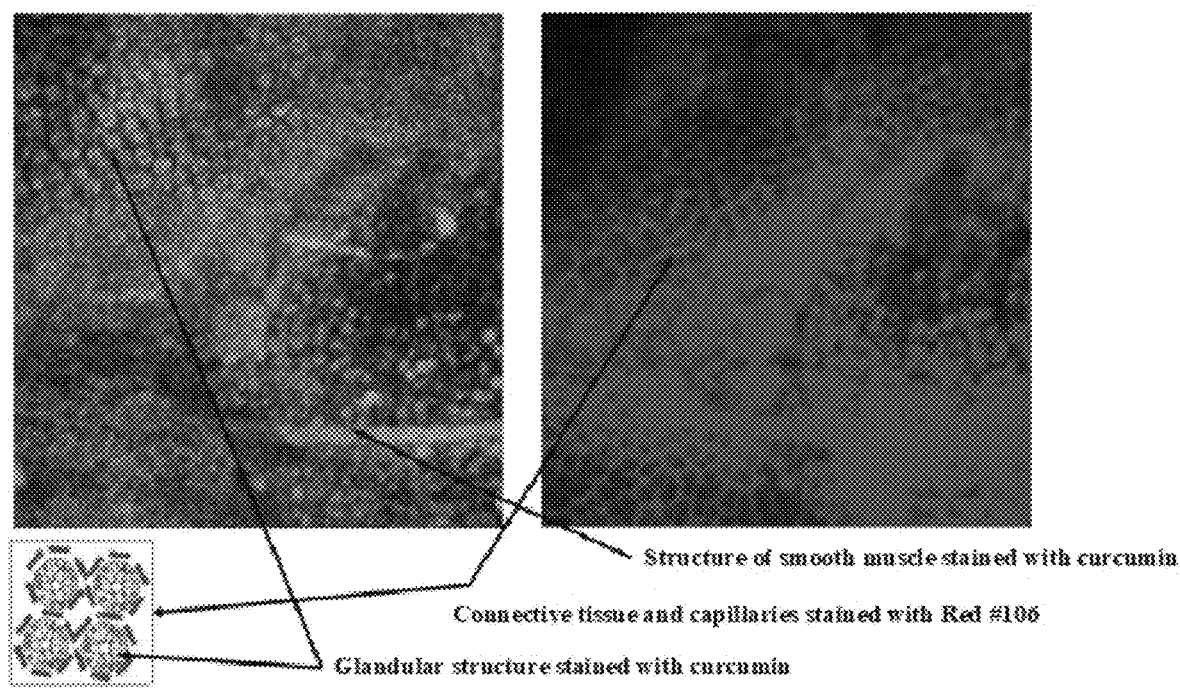
Figure 7:
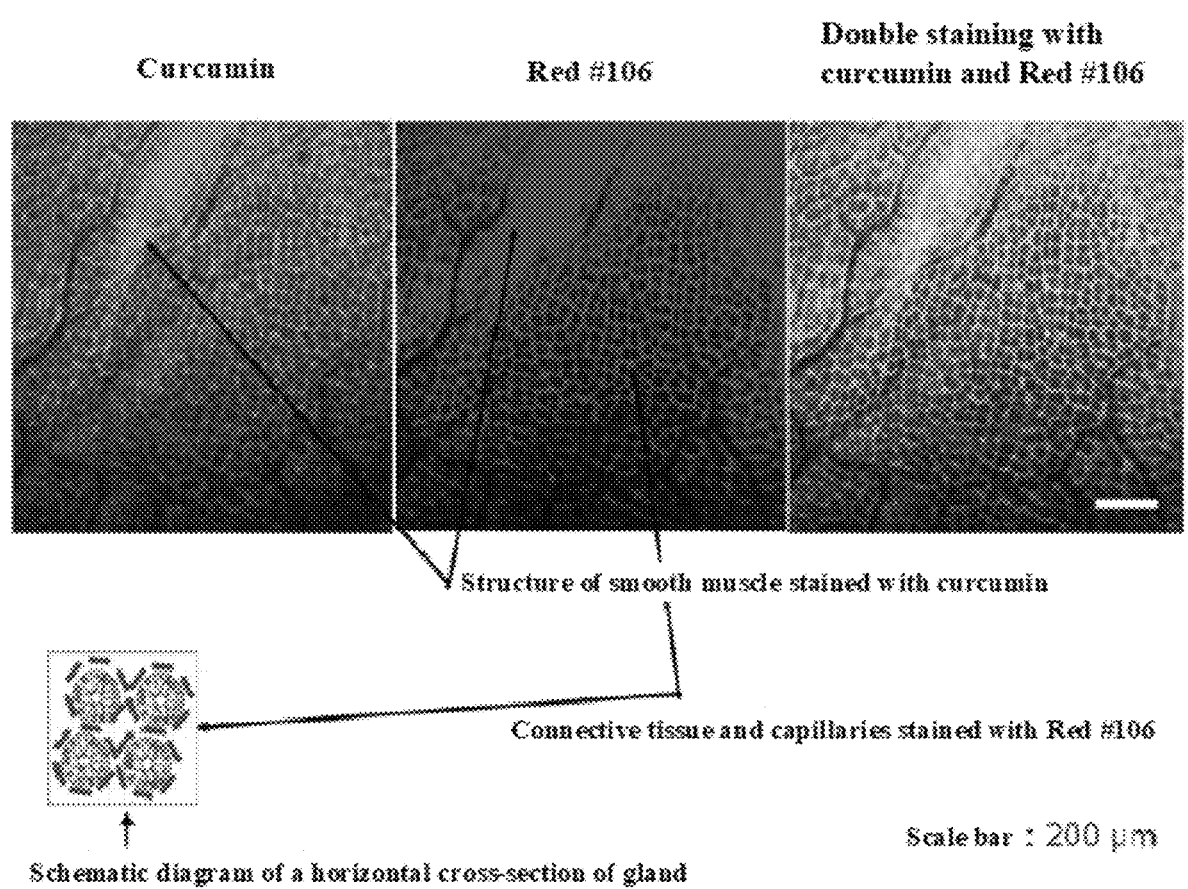
FIG. 7 shows photographs taken with a confocal laser microscope from luminal side by focusing on epithelial and glandular layers (1) and muscularis mucosae (2) (see FIG. 5a) after incising the abdomen of a mouse and staining the tissue of large intestine with curcumin and Red #106 from luminal side of the large intestine (normal tissue). As indicated by the figure, also in the case of staining from luminal side, smooth muscle (muscularis mucosae) is stained by curcumin, while connective tissues and capillaries are stained by Red #106.

In an embodiment of the present invention, Auerbach's plexus in muscle layer can be observed with a multiphoton laser microscope. FIG. 5e is a diagram in which Auerbach's plexus in a muscle layer was visualized by staining with curcumin. In the multiphoton laser microscope image, many tomographic images can be superimposed, so that the network structure of Auerbach's plexus can be visualized in a wider extent.

In an embodiment of the present invention, by vital staining with Red #106, thick blood vessels and smooth muscle can be visualized. A stained isolated large intestine (normal mucosal tissue) of a mouse was photographed from serosal side with a multiphoton laser microscopy by focusing on the muscle layer (4) (see FIG. 5a). It is shown that smooth muscle and vessel walls are stained.

In an embodiment of the present invention, a tissue stained with Red #106 was imaged from serosal side with a multiphoton laser microscope. Structures of gland and crypt can be visualized. FIG. 5g was taken by focusing on epithelial and glandular layers (1) (see FIG. 5a). From the image obtained, because the connective tissue and capillaries are stretching around the gland cells in a circumferential pattern, the distribution pattern of structures of gland and crypt is visualized. This regular distribution pattern of structures of gland and crypt is a major feature of tissue structure of normal large intestine. When a cancer develops, the structures of gland and crypt at a cancer site lose their regularity.

As described above, when a normal mucosal tissue of large intestine of a mouse is imaged with a confocal laser or a multiphoton laser microscopic endoscope by the method of the present invention, among the epithelial and glandular layers (1), muscularis mucosae (2), submucosal layer (3), muscle layer (4) and serosa (5) in the five-layer structure of normal large intestine, curcumin was found to stain glandular cells in epithelial and glandular layers (1) severely positive, the smooth muscle in muscularis mucosae (2) severely positive, the smooth muscle in muscle layer (4) mildly positive, Auerbach's plexus inside muscle layer severely positive, while Red #106 was found to stain a network structure of capillaries surrounding the glandular structures of epithelial and glandular layers (1) severely positive, the smooth muscle in muscularis mucosae (2) mildly positive, the smooth muscle in muscle layer (4) mildly positive, and the wall of a thick blood vessel inside muscle layer severely positive. The visualization of the five-layer structure and major cell structures of normal large intestine by these vital stains is a very useful clue for determining the extent of cancer invasion as follows. That is, presence of a cancer can be determined by combinations of the finding that the above normal structure does not exist at normal sites and the finding that cells which do not exist in the case of normal structure exist.

Figure 8:
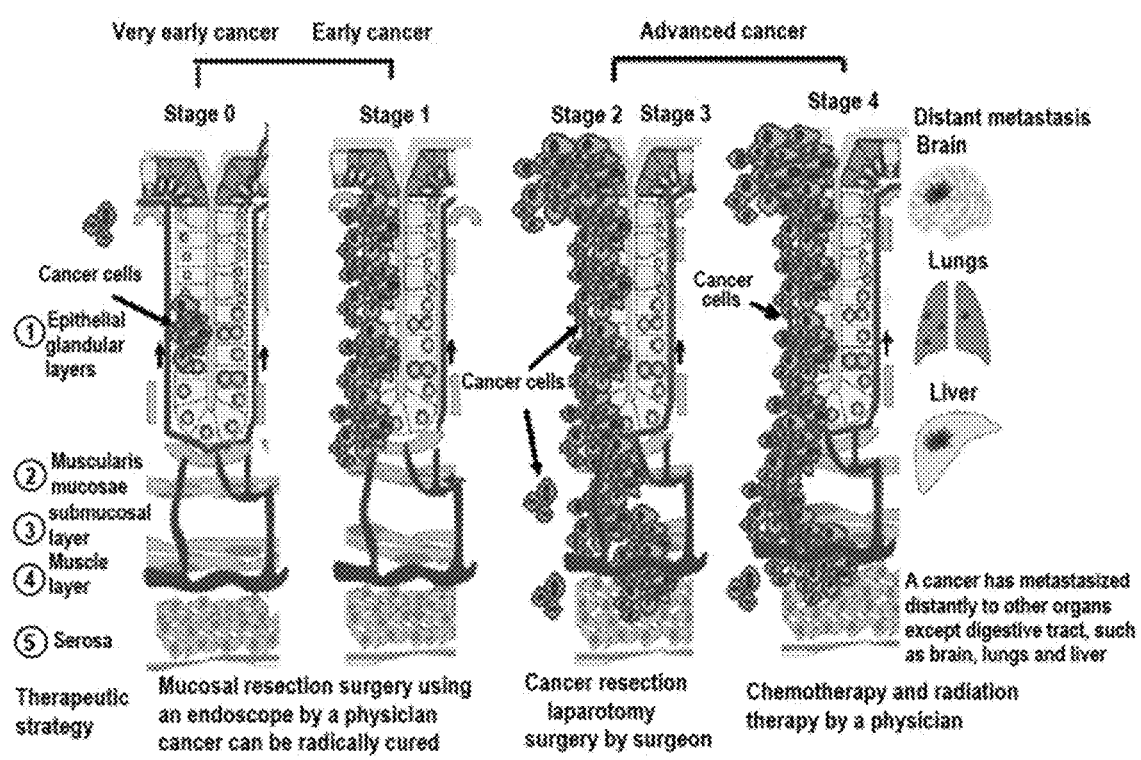
FIG. 8 is a schematic diagram showing staging due to local invasion and metastasis of cancers and treatment strategy.

The judgement on degrees of cancer progression due to local invasion and metastasis and the treatment policy will be described with reference to FIG. 8. A cancer is generally cells located at gland base. It is considered that a cancer is caused by that undifferentiated cells that undergo cell division and proliferation even in a normal state undergo stepwise gene mutation shown in FIG. 1, and that cell division and proliferation are abnormally enhanced. The stage wherein cancer cells do not exit epithelial cells is defined as intraepithelial stage 0 or very early stage of cancer. The stage wherein cancer cells proliferate beyond the area where epithelial cells originally exist in the area where they occurred, but do not cross the muscularis mucosae is defined as stage 1 or early stage of cancer. The stage wherein cancer cells invade the submucosal and muscle layers beyond the muscularis mucosae is defined as stages 2~3. The stage wherein cancer cells have spread to other organs beyond local tissue or organ where they occurred is defined as stage 4. In general, treatment methods mainly include removal of cancer tissue with endoscopy in a case of stages 0 to 1, removal of cancer tissue by surgery in a case of stages 2 to 3, and chemotherapy, radiation therapy and immunotherapy in a case of stage 4. When removing or resecting a cancer tissue by surgery for a case of stage 2 or 3 cancer, the invasion area of cancer cells and the cancer tissue can be examined from the serosal side by using vital staining and laser endoscopy. The present invention is useful for presenting supportive image data to determine a region to be removed or resected.

Figure 9:
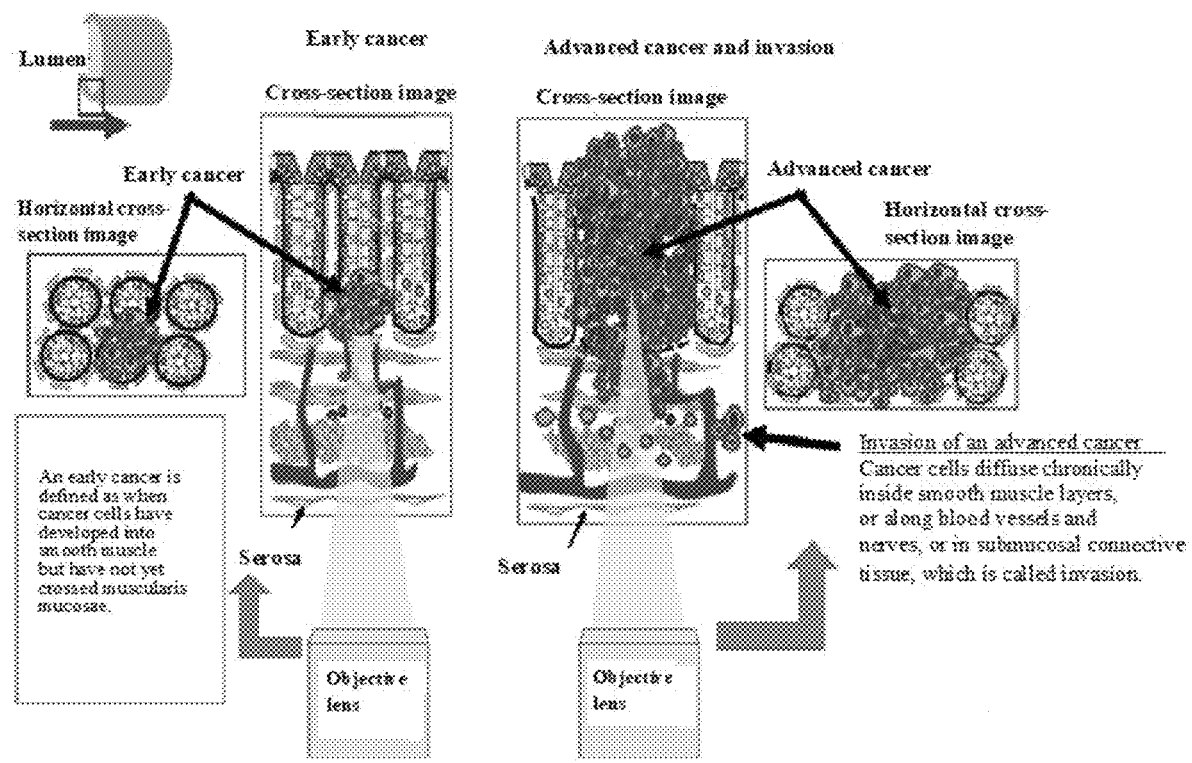
FIG. 9 illustrates cancer cell architecture and local invasion of an advanced cancer.

In a case of local invasion of advanced cancer, cancer cells diffuse chronically along blood vessels and nerves inside smooth muscle layers or in submucosal connective tissue (see FIG. 9). This phenomenon is called local invasion of cancer cells. It is extremely difficult to accurately determine the extent of local invasion by current methods such as close inspection by naked eyes and change in the hardness of a tissue by palpation.

Figure 10A:
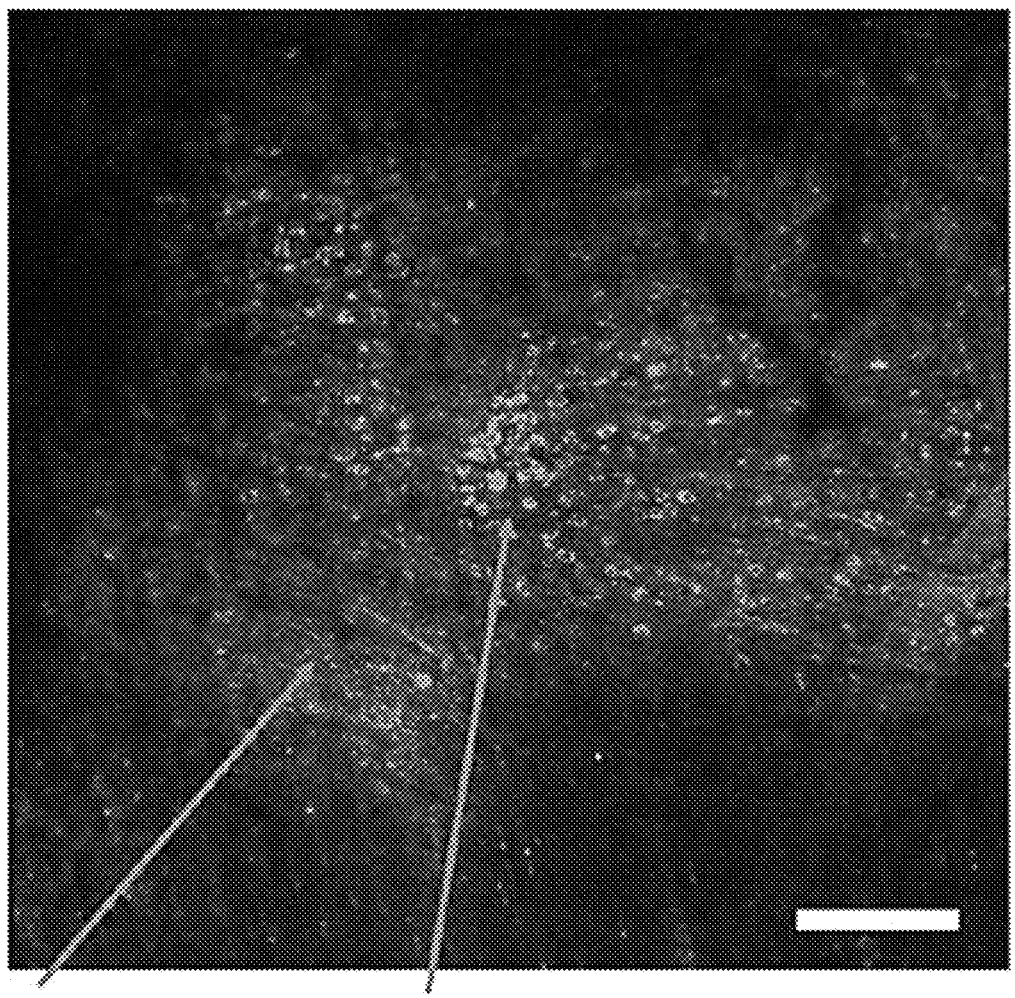
FIG. 10A and FIG. 10B are photographs taken with a confocal laser microscopy from serosal side after incising the abdomen of a colon cancer mouse, and staining the tissue of large intestine from the serosal side of the large intestine (cancer tumor site) with curcumin. The two arrows in FIG. 10A indicate smooth muscle layer and cancer cells, respectively. The three arrows in FIG. 10B indicate blood vessels, smooth muscle layers, and cancer cells, respectively.
Figure 10B:
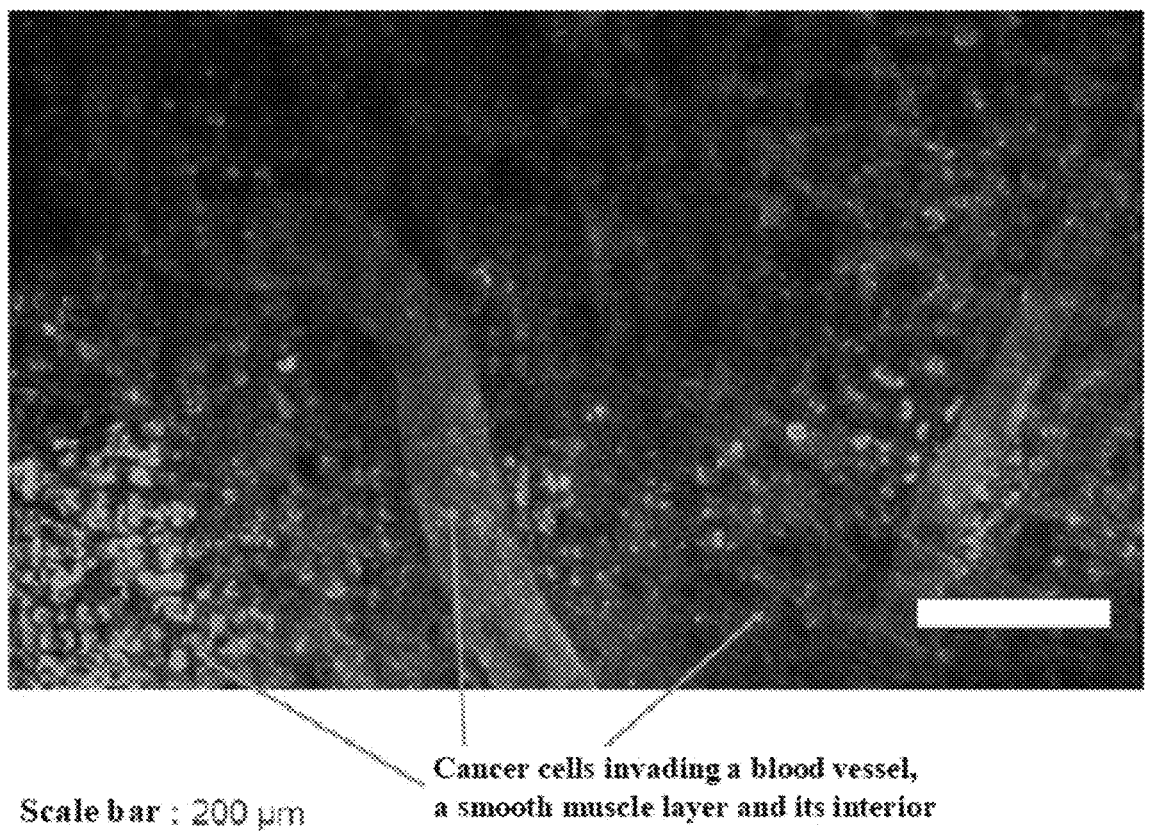

However, the presence of cancer cells can be clearly recognized by staining a cancer tumor site in a colon cancer mouse with curcumin from serosal side and observing from the serosal side with a confocal laser microscope. Referring to FIG. 10A, a large number of large cells positive for curcumin staining are scattered chronically inside the smooth muscle layer. These cells are judged to be invaded cancer cells. In addition, since the cytoplasm of these cells is darker than surrounding tissues by curcumin staining and recognized as a positive image, these cells are judged to be cancer cells. That is, these cells are judged to be cancer cells by the finding that cells that should not exist in a normal case exist in places where they should not exist. Referring to FIG. 10B, cancer cells invading blood vessels and a smooth muscle layer are observed. The fact that some cancer cells aggregate around blood vessels suggests that cancer cells have the property of moving along blood vessels and infiltrating.

Figure 11A:
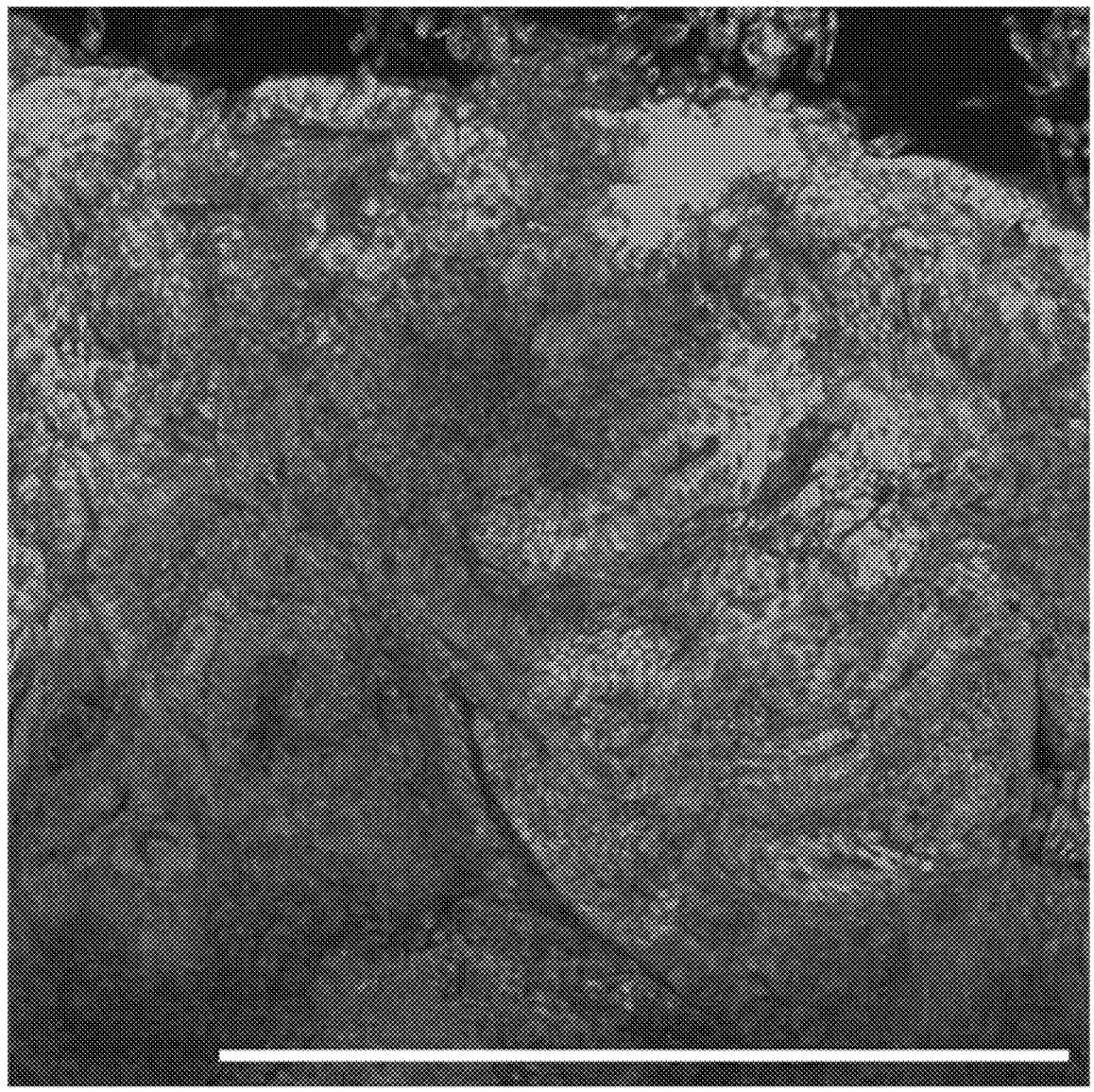
FIG. 11A and FIG. 11B are photographs taken with a multiphoton laser microscope from luminal side after incising the abdomen of a colon cancer mouse, and staining the tissue of large intestine (cancer tumor site) with curcumin from the luminal side.
Figure 11B:
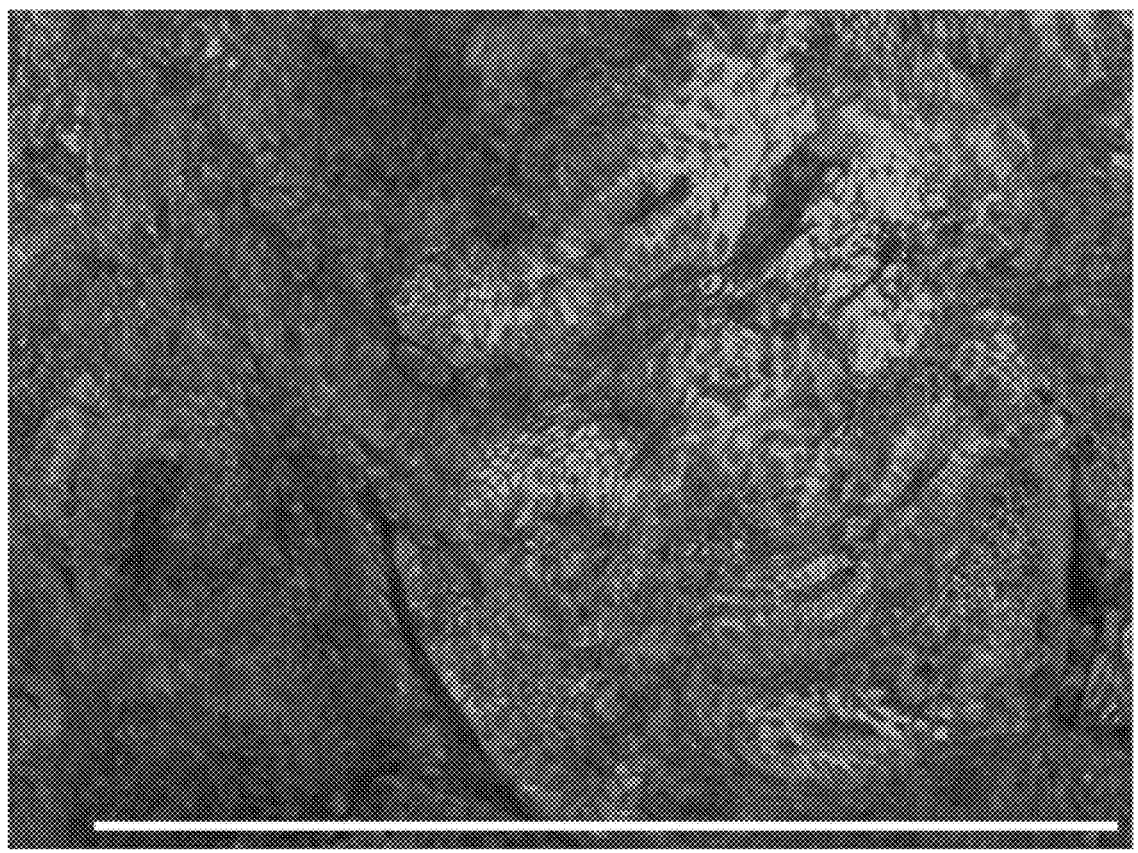

FIG. 11A and FIG. 11B are photographs taken from luminal side of a tumor site of a colon cancer mouse, after staining with curcumin from the luminal side. As indicated by these photographs, in cancer cells, cytoplasm is stained severely, while nuclei are stained negatively. As a result, cellular atypia and structural atypia of a cancer can be distinguished.

Figure 12:
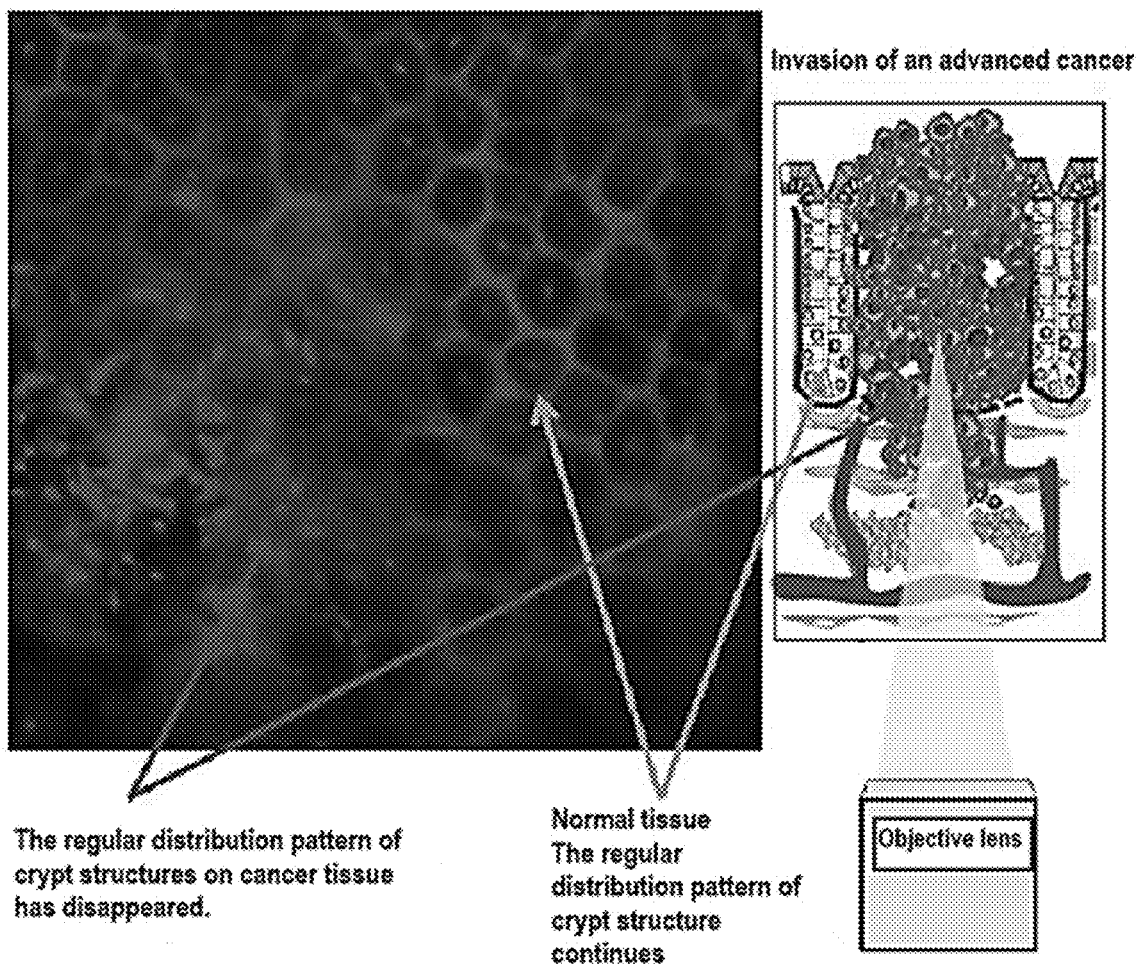
FIG. 12 is a photograph taken with a multiphoton laser microscope from serosal side after incising of the abdomen of a colon cancer mouse, and staining the tissue of large intestine (cancer tumor) with Red #106 from the serosal side.

FIG. 12 shows a photograph of a cancer tumor site of a colon cancer mouse taken from serosal side with a multiphoton laser microscope, after staining with Red #106 from the serosal side, and a schematic view of advanced cancer invasion. In normal tissue, it can be confirmed that the crypt structure is regularly distributed. On the other hand, in cancer tissues, the regular distribution of crypt structure has disappeared, and the case can be judged as cancer. That is, it is determined that cancer cells are present at this site because a normal structure is not at its normal site.

Figure 16:
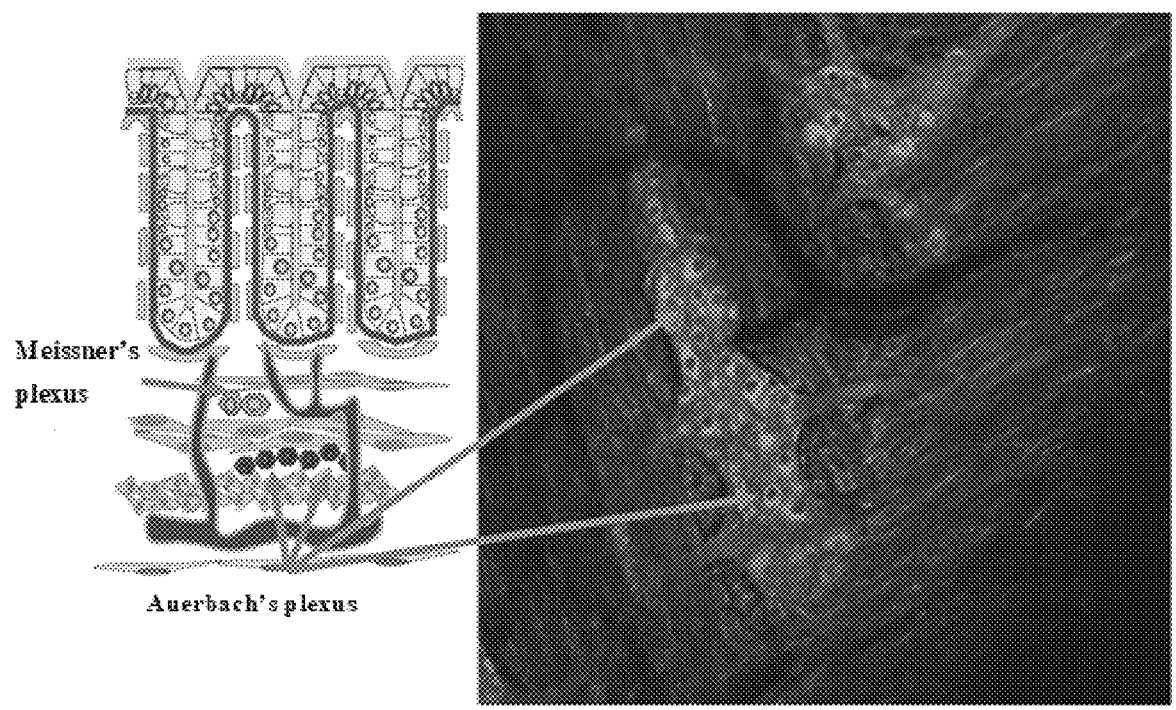
FIG. 16 is a diagram showing, at high magnification, an example of visualization with a laser microscope of Auerbach's plexus in muscle layer after vital staining from serosa side with curcumin.

In an embodiment of the present invention, Auerbach's plexus in muscle layers can be visualized by a laser microscope after vital staining with curcumin. FIG. 16 is an example in which large intestine of a mouse was stained with curcumin from serosal side, and then Auerbach's plexus in a muscle layer was visualized by a laser microscope. Based on FIG. 16, the perikaryon can be identified by curcumin staining. Curcumin stains only the cytoplasm, but does not stain the nucleus in perikaryon, so that the cytoplasm is viewed as a positive image and the nucleus is viewed as a negative image. Accordingly, the morphology of perikaryon can be accurately determined. Cancer cells develop in the epithelial and glandular layers (1) (see FIG. 5a), and then expand and move to other layers. (which is called cancer cell invasion) In that case, it is known that cancer cells tend to move along blood vessels and peripheral nerves. Therefore, the ability to visualize Auerbach's plexus in muscle layer by the vital staining of curcumin indicates that the invasion pathway of cancers can be visualized, which is useful for determining the extent of cancer invasion. In addition, early cancers and advanced cancers can be determined.

Figure 17:
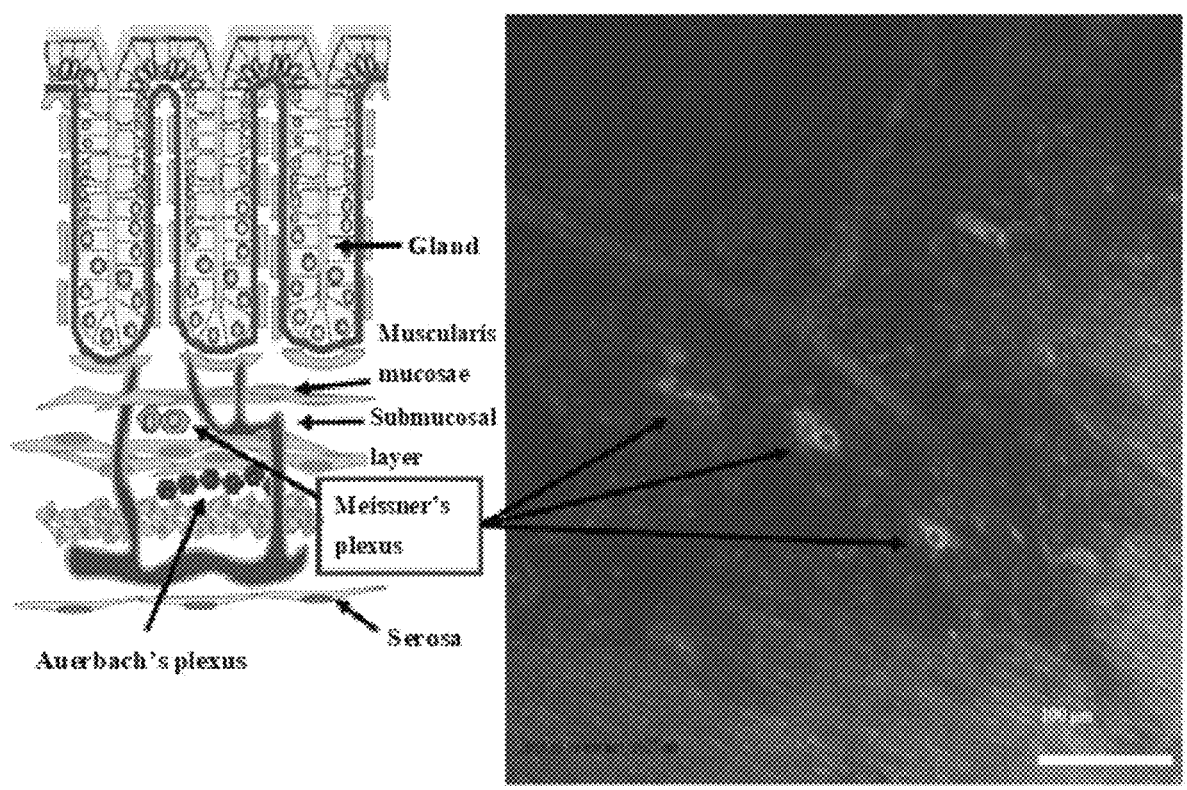
FIG. 17 is a diagram showing, at high magnification, an example of visualization with a laser microscopy of autonomic plexus in the muscle layer (Meissner's plexus) after vital staining from serosa side with curcumin, based on which perikaryon can be identified.

In an embodiment of the present invention, autonomic plexus in muscle layer (Meissner's plexus) can be visualized with a laser microscope after vital staining with curcumin. FIG. 17 shows an example in which Meissner's plexus was visualized with a laser microscope after staining large intestine of a mouse with curcumin from serosa side. Based on FIG. 17, perikaryon can be identified by curcumin staining. The Meissner's plexus is located in submucosa, and one to several neuronal cells form a group. Curcumin stains only the cytoplasm, but does not stain the nucleus in perikaryon, so that the cytoplasm is viewed as a positive image and the nucleus is viewed as a negative image. Accordingly, the morphology of perikaryon can be accurately determined.

Figure 18:
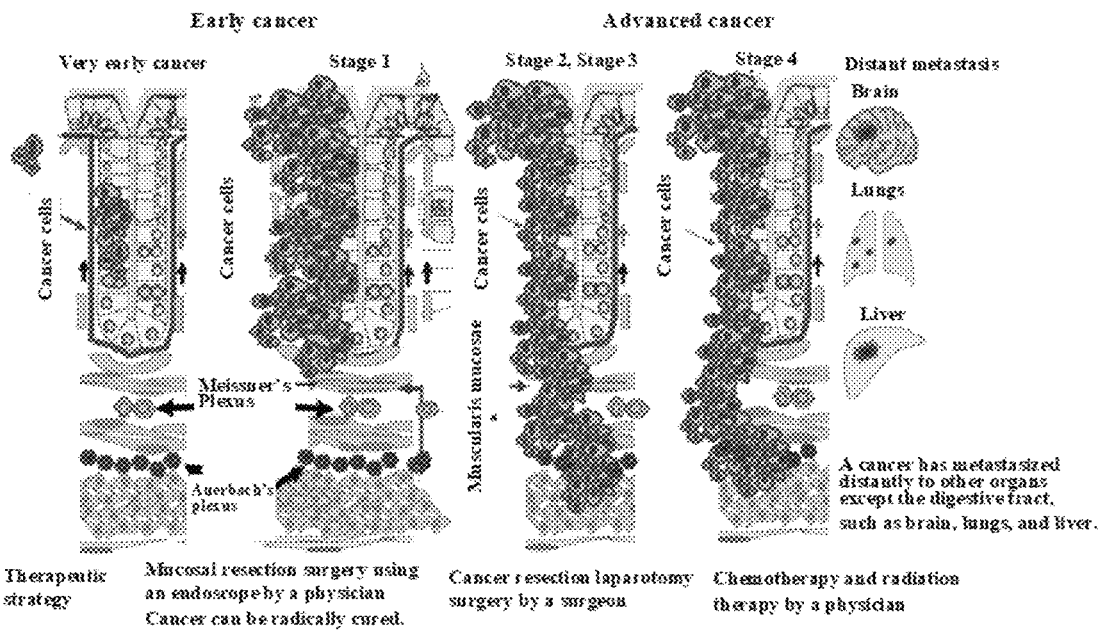
FIG. 18 is a diagram schematically showing the process of cancer cell invasion and stage classification of cancers.

With reference to FIG. 18, a primary lesion necessarily remains inside mucosal epithelium, because cancers generally arise from mucosal epithelial cells. When the cancer tissue grows, cancer cells invade from inside the mucosal epithelium to deep parts. If the cancer cells have not yet invaded or reached the muscularis mucosae and Meissner's plexus, the cancer is judged as an early cancer. On the other hand, if the cancer cells have invaded or reached Meissner's plexus and smooth muscle layer, the cancer is judged as an advanced cancer.

Figure 19:
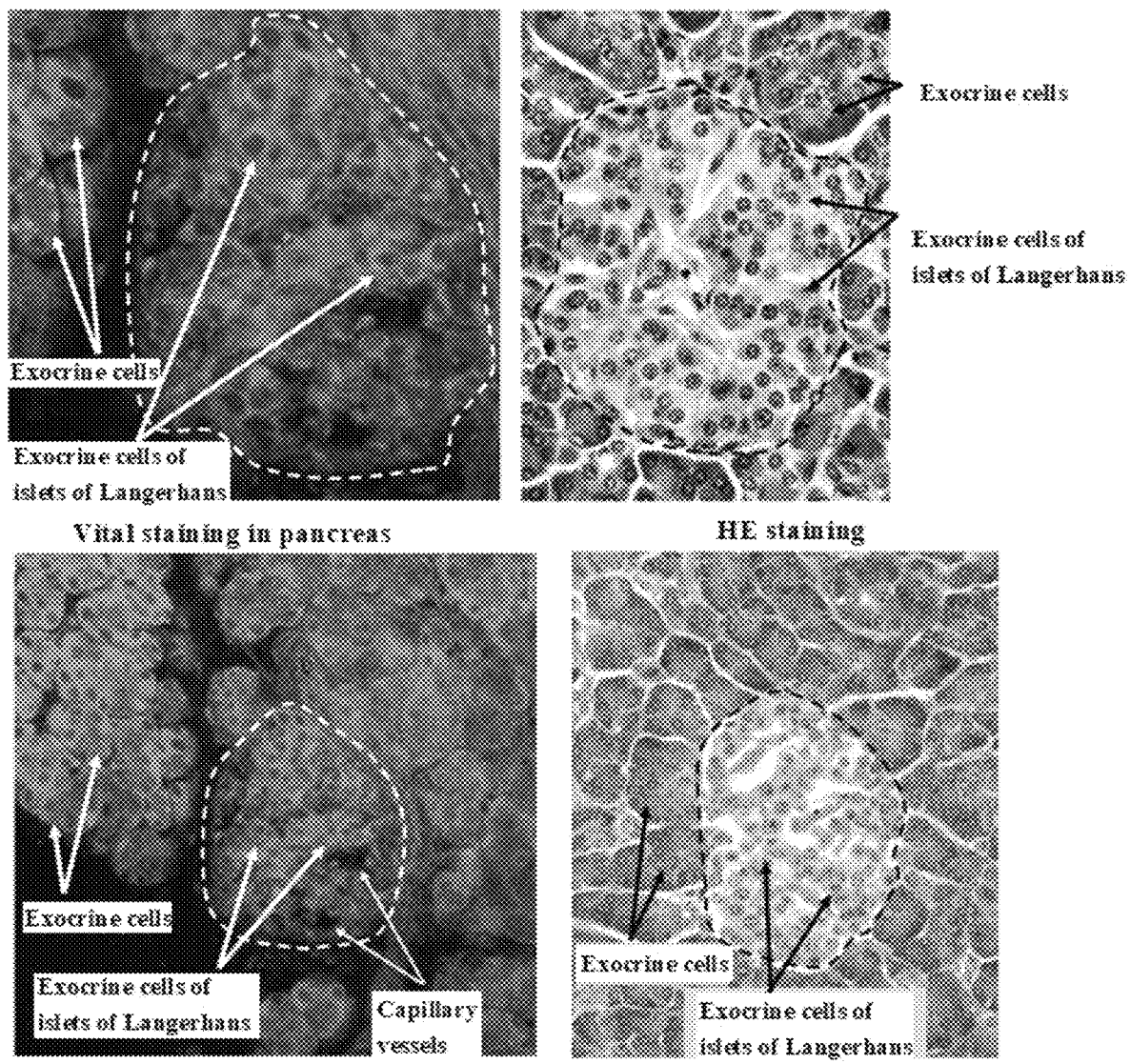
FIG. 19 shows, at high magnification, examples of visualization with a laser microscope of exocrine cells and islets of Langerhans of pancreas after vital staining by intraperitoneal administration of curcumin. Furthermore, it shows hematoxylin-eosin (HE) staining images of a pancreatic tissue.

According to the present invention, various living tissues can be visualized. FIG. 19 is a diagram in which exocrine cells of pancreas and islets of Langerhans are visualized with a laser microscope after vital staining by intraperitoneal administration of curcumin to a mouse. FIG. 19 further shows hematoxylin-eosin (HE) staining images of pancreatic tissues. As a result, exocrine cells and endocrine cells of islets of Langerhans (within the dashed line) can be distinguished based on cell size and sequence. It can be seen that the endocrine cells are small, dozens of them aggregate in a globular shape, and the inside is rich in capillaries. Exocrine cells are larger than endocrine cells, and have a large number of secretory granules inside, which are clustered in groups of several cells. By intraperitoneal administration of a sterilized curcumin solution, the islets of Langerhans in pancreas can be visualized, so that it can be used for diagnosis of diabetes and insulinoma in endocrine region.

Figure 20:
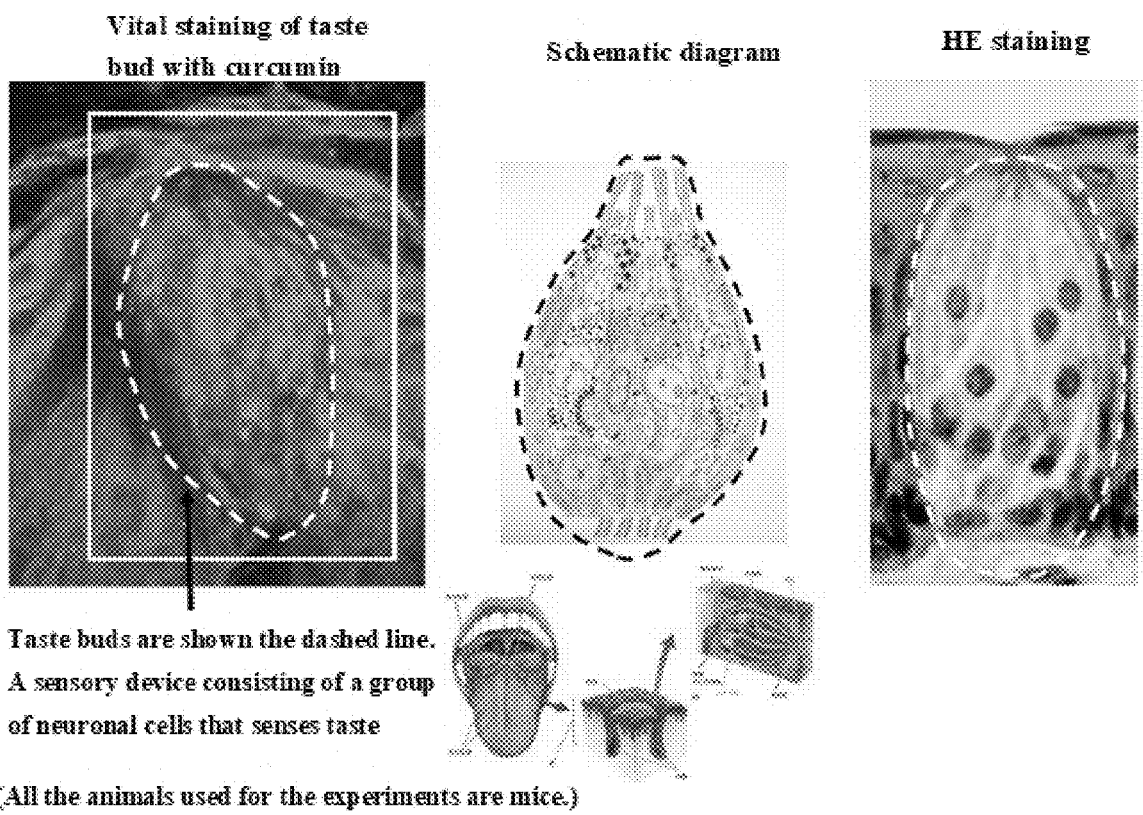
FIG. 20 is a diagram showing, at high magnification, an example of visualization with a laser microscope of a taste bud, which is a taste sensory device, after vital staining by coating curcumin onto tongue mucosa.
Figure 21:
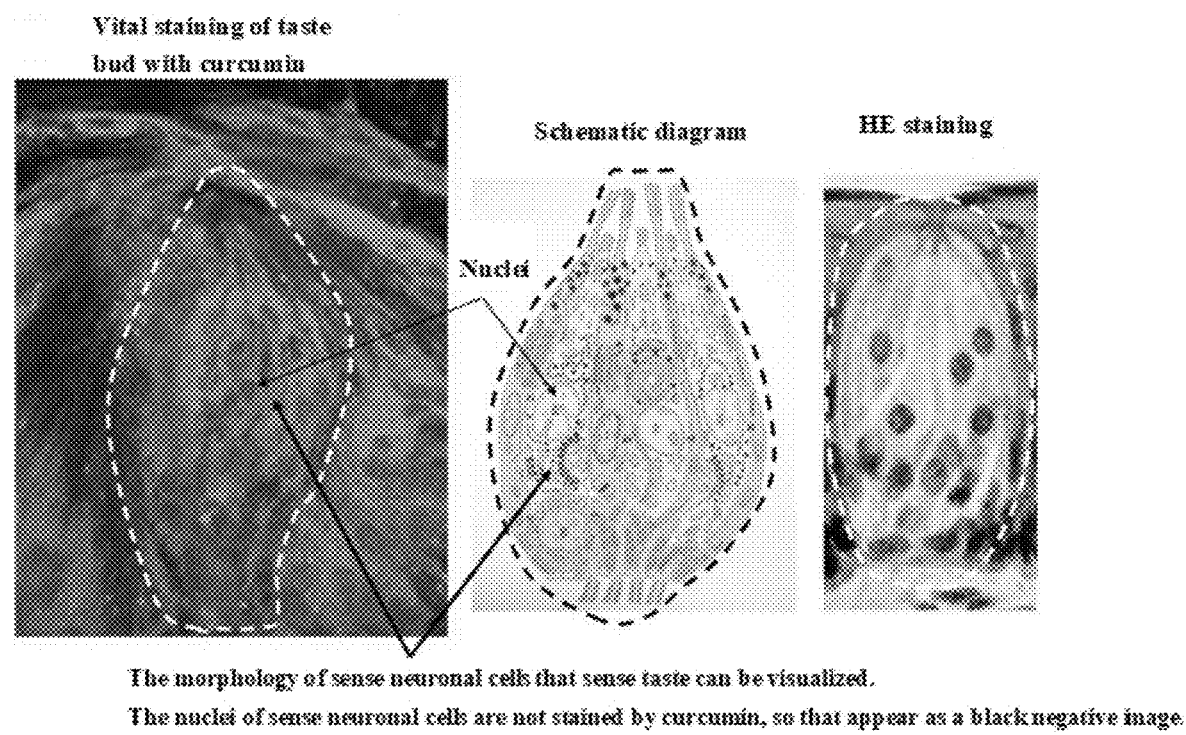
FIG. 21 is a diagram showing, at high magnification, an example of visualization with a laser microscope of a taste bud, which is a taste sensory device, after vital staining by coating curcumin onto tongue mucosa.

FIG. 20 to FIG. 22 are diagrams in which a taste bud, which is a taste sensory device, is visualized by a laser microscope after vital staining by coating curcumin on mouse tongue mucosa. FIG. 20 and FIG. 21 further show hematoxylin and eosin-stained images of taste buds. The nuclei of sensory neuronal cells are not stained with curcumin, so that they are recognized as black negative images. By coating curcumin on oral mucosa, the neuronal cells of a taste bud, which is a taste sensory device, can be visualized, so that a taste disorder can be examined in otolaryngologic field.

Figure 23:
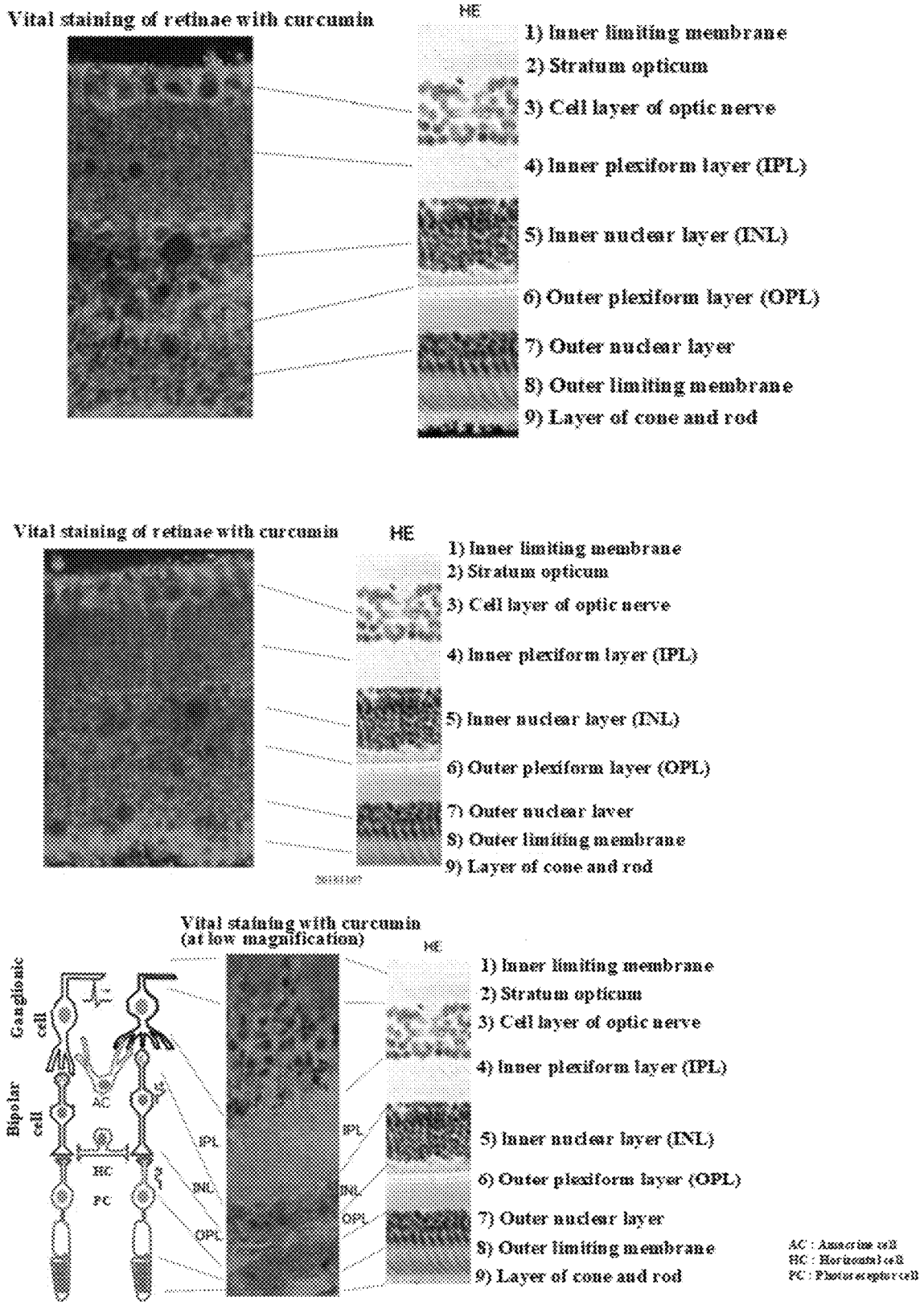
FIG. 23 is a diagram showing, at high magnification, examples of visualization with a laser microscope of a retinal neuronal cell group after vital staining by intraperitoneal administration of curcumin.
Figure 24:
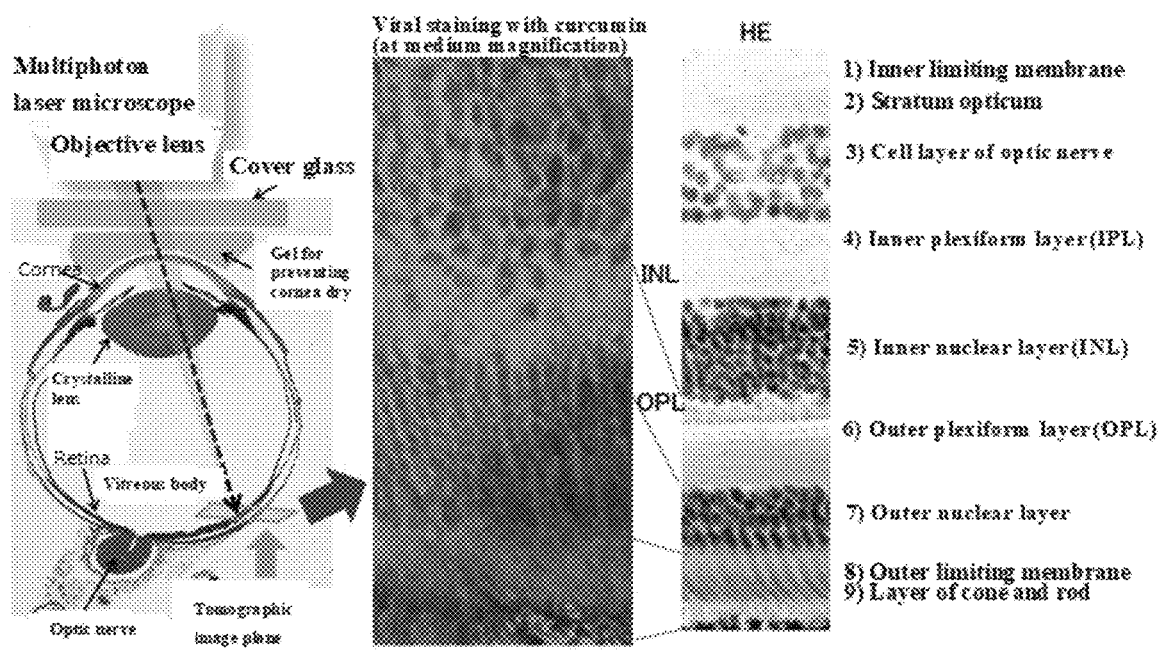
FIG. 24 is a diagram showing, at high magnification, an example of visualization with a laser microscope of a retinal neuronal cell group after vital staining by intravitreal injection of curcumin.

FIG. 23 and FIG. 24 are diagrams in which a retinal neuronal cell group was visualized with a laser microscope after vital staining by intraperitoneal administration of curcumin to a mouse. These figures include hematoxylin and eosin staining images of retinal tissue. As indicated by the figures, retinal neuronal cell groups and synapse can be visualized. By oral administration or intravitreal injection of curcumin, membrane neuronal cell groups and synapses can also be visualized. In ophthalmic field, for example, the stage of diabetic retinopathy, macular degeneration, retinal degeneration, proliferative vitreoretinopathy, glaucoma, or edema retinoblastoma can be determined.

Furthermore, olfactory nerve fibers (FIG. 25) and olfactory receptor neurons that are odor sensory cells (FIG. 26) can be stained with curcumin and visualized with a laser microscope. A hematoxylin-eosin staining image is shown in FIG. 26. The cytoplasm of olfactory receptor neurons and cilia having odor receptors are stained positively with curcumin. Since a nucleus is not stained, it is viewed as a black negative image. By coating curcumin on nasal mucosa, olfactory receptor neuronal cells, which are odor sensing cells, can be visualized, so that olfactory disorders can be examined.

In an embodiment of the present invention, the thyroid can be visualized with a laser microscope after vital staining with curcumin (FIG. 27). The structure of vesicles is stained by vital staining thyroid with curcumin. Thyroid is formed by spherical follicles of various sizes. These follicles are bordered by a monolayer of squamous or cubic epithelium, and are filled with colloid that is evenly stained with hematoxylin and eosin in lumen. It can be seen that the periphery of the vesicle is surrounded by a dense capillary network.

In an embodiment of the present invention, actin/myosin striation, nuclei and myofibers of skeletal muscle can be visualized with a laser microscope after vital staining by coating curcumin onto fascia (FIG. 28). By coating a sterilized solution of curcumin on fascia, myofibers of skeletal muscle and actin molecules can be visualized, so that it can be possibly applied to morphological photo biopsy diagnosis of muscle weakness/Frail syndrome.

In an embodiment of the present invention, the structure of bright center and dark shell of the secondary nodules of lymph nodes can be visualized with a laser microscope after vital staining by coating curcumin onto lymph nodes (FIG. 29). In the bright center, many cells with large bright nuclei can be observed. These cells are reticulum cells and large lymphocytes which are undergoing cell division. The dark shells have a structure in which small lymphocytes proliferating in the bright center accumulate around the bright center. The cell structure inside lymph node can be visualized by coating a sterilized solution of curcumin to the surface. Accordingly, in urology field and gastrointestinal surgery field, it is possible to determine the presence or absence of lymph node metastasis of cancers during laparoscopic robotic surgery.

Figure 30:
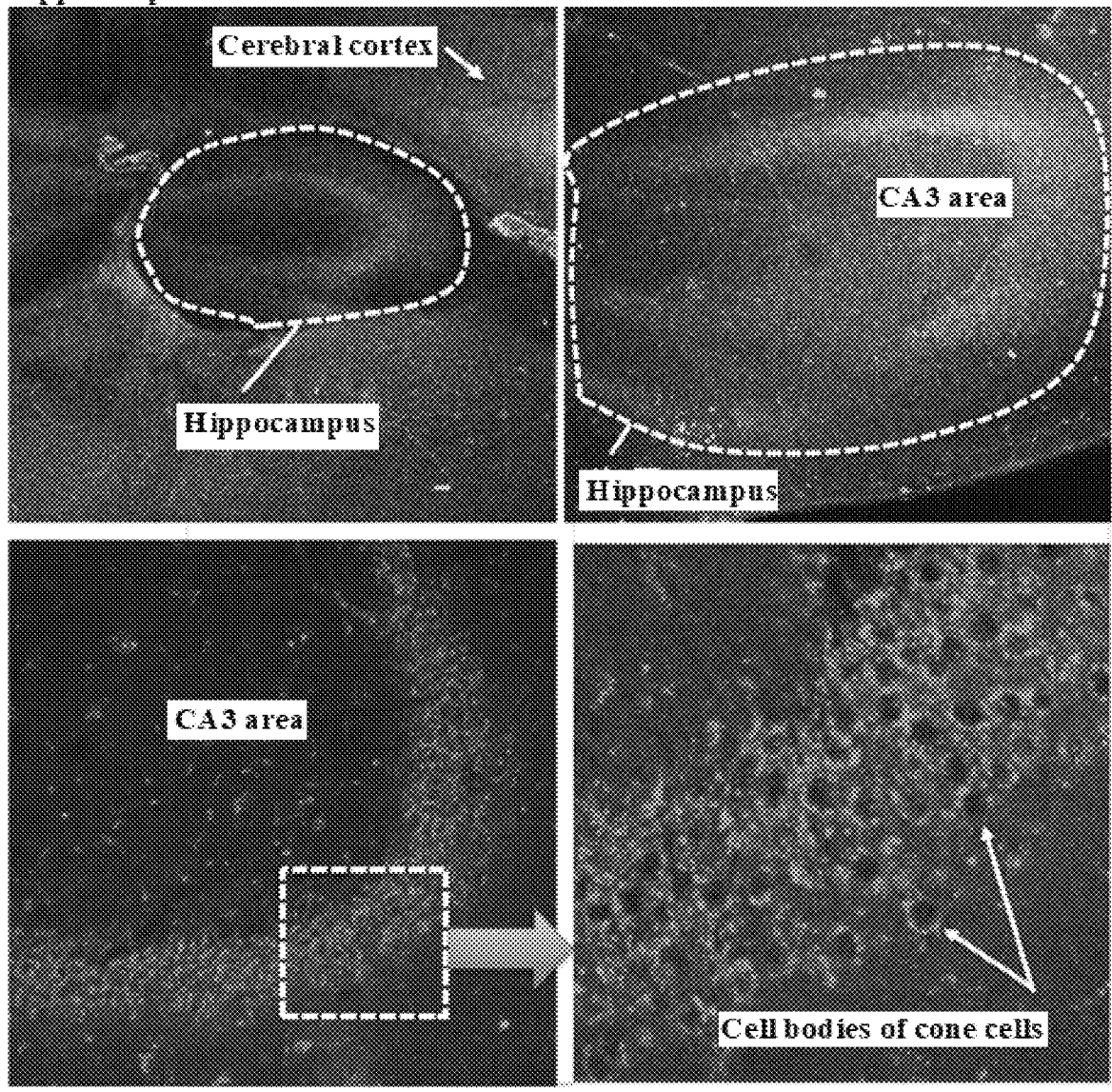
FIG. 30 shows visualization with a laser microscope of cell bodies of hippocampal neurons after intraperitoneal administration of curcumin to a mouse.
Figure 31:
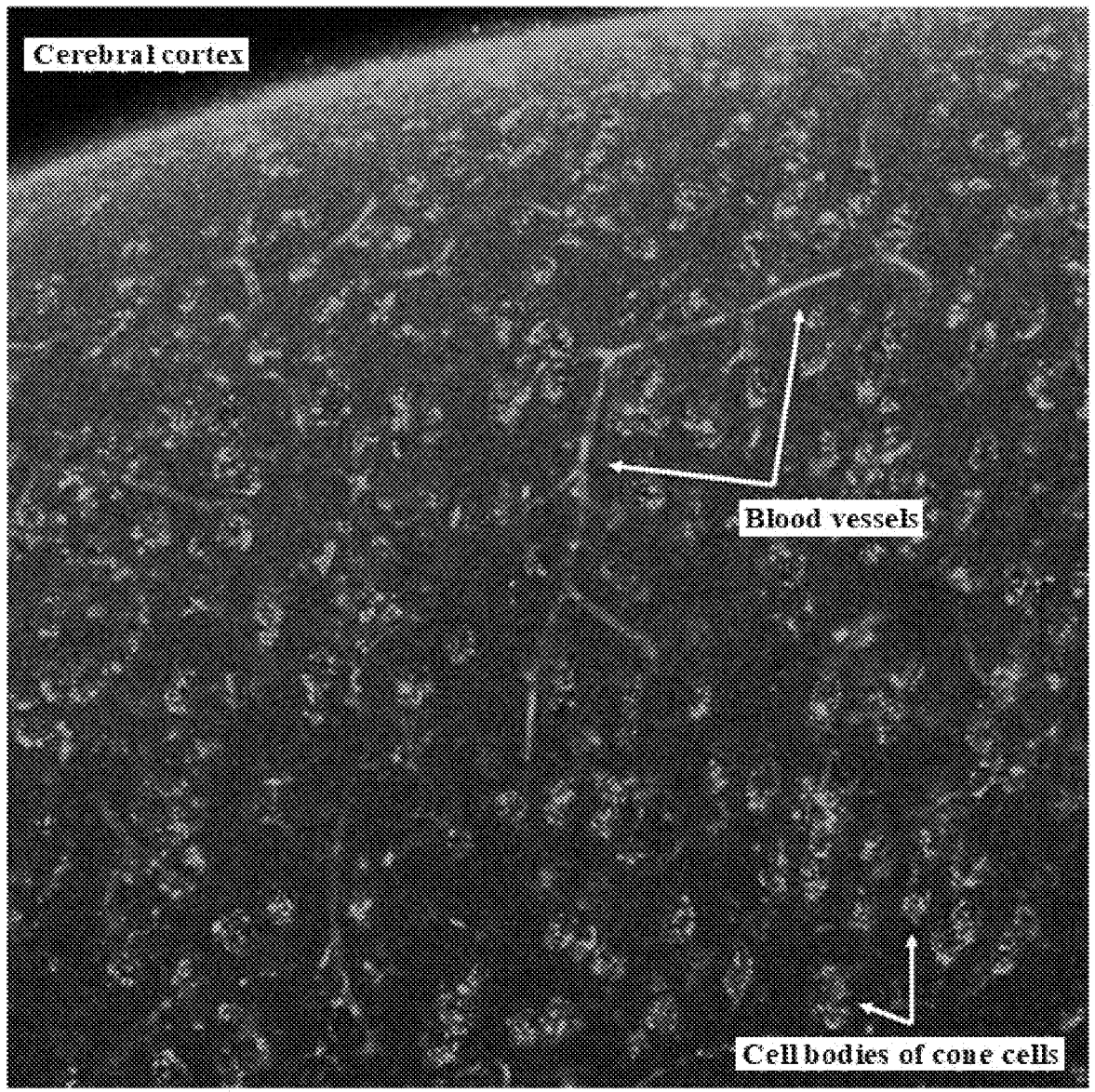
FIG. 31 shows visualization with a laser microscope of cerebral cortex after intraperitoneal administration of curcumin to a mouse.
Figure 32:
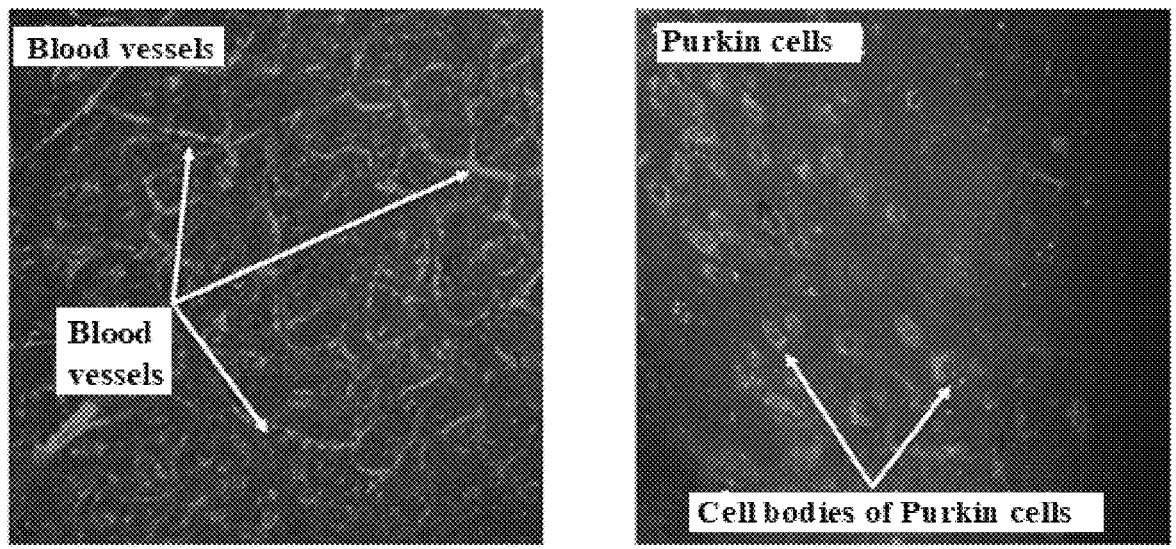
FIG. 32 shows visualization with a laser microscope of cell bodies of neuronal cells in cerebellum and blood vessels after intraperitoneal administration of curcumin to a mouse.

In an embodiment of the present invention, pyramidal cell bodies can be visualized in hippocampal CA3 area by laser microscopy after intraperitoneal administration of curcumin (FIG. 30). In cerebral cortex, cell bodies of blood vessels and cone cells can be visualized (FIG. 31). In cerebellum, cell bodies of blood vessels and Purkin cells can be visualized (FIG. 32). By using the present invention, Alzheimer's disease, cerebral infarction, cerebral hemorrhage, subarachnoid hemorrhage, spinocerebellar degeneration, and the like, which are accompanied by degeneration of brain tissue, can be examined.

According to the present invention, it is possible to determine or diagnose diseases in which morphology, relative position and arrangement in tissues, and number of cells in tissues are changed or fluctuated in all organs compared with normal tissues. The diseases include, but are not limited to, the diseases exemplified above, such as cancer, diabetes, diabetic retinopathy, macular degeneration, retinal degeneration, taste disorder, olfactory disorder, Alzheimer's disease, and cerebral infarction, etc. On the other hand, diseases in which only the function of cells changes or fluctuates, for example, schizophrenia, cannot be determined or diagnosed by the present invention.

The method of the present invention is characterized in that by performing tissue staining and laser irradiation from serosal side of an organ suspected of having cancer, cancer tissue can be visualized before surgery or before resection of an affected part during surgery. In actual surgery, visualizing the location or invasion extent of cancer cells and marking the resection site of an organ, that is, the margin of the cancer tissue is greatly supportive for a surgeon. For this purpose, it is preferable to color the location or invasion extent of the cancer cells on serosa. For such coloring, a surgical thread or tape may be used as a well-known surgical biomarker, or a marking dye may be used. Examples of surgical biomarkers include sodium sulfobromophthalein, indocyanine green, sodium fluorolein, methylene blue, indigo carmine, toluidine blue, and picotanine blue, etc. To enhance tissue adhesion of these marking dyes, a thickener such as sodium carboxymethylcellulose, sodium hyaluronate, gum arabic, and the like can be mixed.

As a tip probe for laser irradiation, a stick type objective lens having a diameter of about 5 mm and a needle type objective lens having a diameter of about 0.3~2 mm can be used in addition to a normal objective lens having a diameter of about 20 mm.

During a surgical operation for cancer treatment, notifying operators that cancer cells have been detected is useful as a supportive method for assisting operators in successfully performing cancer treatment. Such notification to the operators can be made by sound or light. In particular, a system for notifying the presence of a cancer tissue by comparing images photographed with a laser microscope with cancer tissue images stored in a database in advance is preferable as a means for preventing cancer tissue from being left behind.

The test conditions in the above tests, that is, the preparation of cell staining solutions, the animals used, the methods for preparing model mice with colon cancer, and the conditions of laser irradiation are as follows.

[Preparation of Cell Staining Solutions]

100 mg of curcumin (Tokyo Kasei, cat. #C2302, purity 97.0%) was suspended in 5 mL of ethanol, and further diluted 10-fold with ethanol. It was mixed with the same amount of glycerin, and further diluted 10-fold with glycerin. The mixture was mixed with the same amount of purified water to obtain a staining solution of curcumin. As for Red #106, its staining solution is obtained by dissolving the powder in saline to the concentration of 1 mg/mL.

[Animals]

C57BL/6N mice purchased from Japan SLC, Inc. were used in the tests. All tests were performed on male, 8-week-old mice weighing 20~25 grams.

[The Methods for Preparing Model Mice with Colon Cancer]

Model mice with colon cancer were prepared by intraperitoneally administering 10 mg/kg of azoxymethane (AOM) dissolved in saline 4 times at weekly intervals to C57BL/6N mice.

[Conditions of Laser Irradiation]

A multiphoton laser microscope of FVMPE-RS (Olympus) was used with the irradiation wavelength of 800 nm. Laser irradiation was performed at 5.8~48.2% of its full power output. A confocal laser microscope of FV1000 (Olympus) was used with the irradiation wavelength of 488 nm and 594 nm, wherein the laser irradiation at 488 nm was performed at 1~529.4% of its full power output, and the laser irradiation at 594 nm was performed at 13~13.5% of its full power output. The direction of irradiation and staining from serosal or luminal side are described in the figures.

Figure 14:
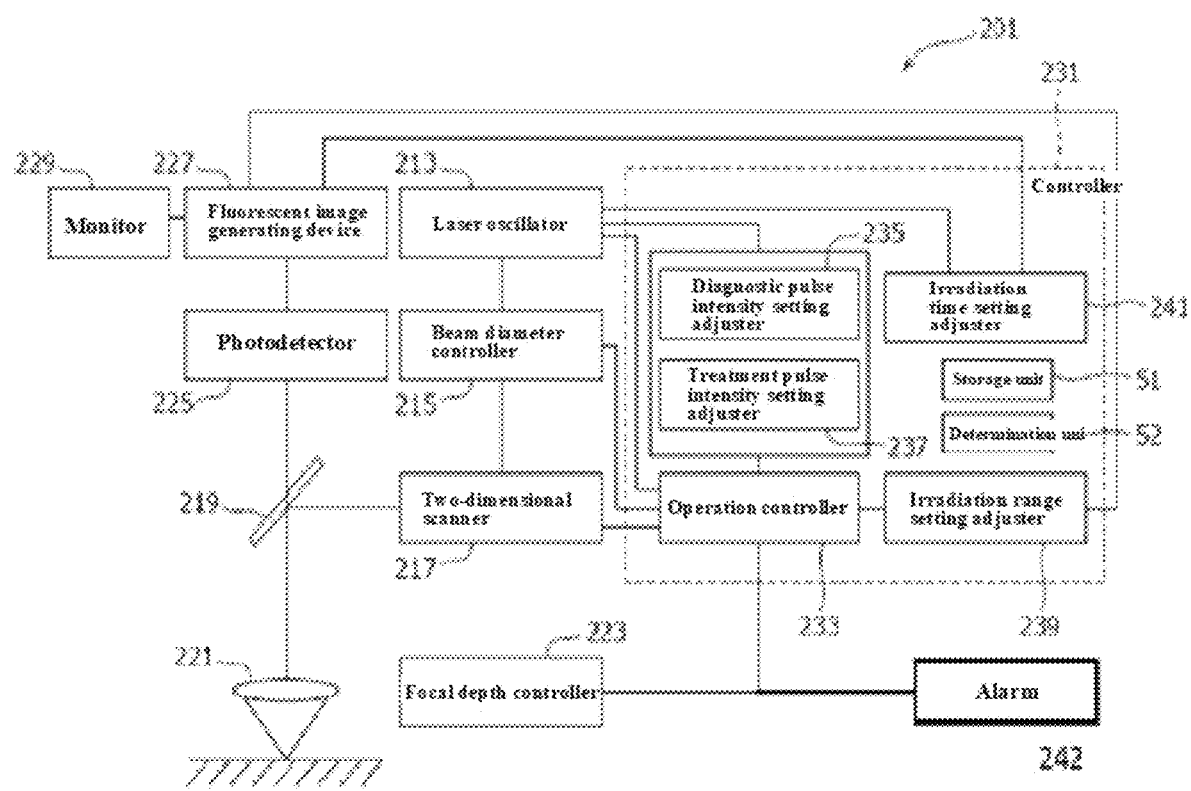
FIG. 14 is a diagram showing a cancer test device (201) according to the present embodiment.

In an embodiment of the present invention, as shown in FIG. 14, the cancer testing device (201) is equipped with laser oscillator (213), beam diameter controller (215), two-dimensional scanner (217), dichroic mirror (219), objective lens (221), focal depth controller (223), photodetector (225), fluorescence image generating device (227), monitor (229) and controller (231).

As the laser oscillator (213), one capable of adjusting the output of pulsed laser light with a pulse width in the extent of tens to hundreds of femtoseconds and a pulse repetition frequency in the extent of tens to hundreds of MHz is used.

The beam diameter controller (215) is a beam expander that changes the beam diameter of pulse laser light according to a beam diameter adjustment signal from the controller (231).

The two-dimensional scanner (217) comprises, for example, two Galvano mirrors, and changes the focal position of pulsed laser light in two axial directions perpendicular to optical axis.

The dichroic mirror (219) separates the fluorescence generated in a cancer-related gene product of living cells by irradiating with pulsed laser beam.

The objective lens (221) condenses the pulsed laser light emitted from the laser oscillator (213) on living cells, while condensing the fluorescence generated in a cancer-related gene product according to multiphoton absorption phenomenon. The objective lens (221) is movable in optical axis direction by a focal depth controller (223) based on a control signal, and can adjust the focal position.

The photodetector (225) detects the fluorescence generated in a cancer-related gene product and converts it into electric signals corresponding to fluorescence intensity.

The scanning state of the two-dimensional scanner (217) and the adjustment position (position in the depth direction) of the focal depth controller (223) are parameters representing coordinates of focal position. The fluorescence image generating device (227) stores the parameters representing these coordinates and the electric signal (that is, the fluorescence intensity) transmitted from the photodetector (225) in association with each other, processes these data, and generates fluorescence images. A generated fluorescent image is displayed on the monitor (229).

The controller (231) comprises operation controller (233), diagnostic pulse intensity setting adjuster (235), irradiation extent setting adjuster (239) and irradiation time setting adjuster (241). The operation controller (233) controls the operations of the laser oscillator (213), the beam diameter controller (215), the two-dimensional scanner (217) and the focal depth controller (223).

In order to perform a test, a pulse laser beam intensity is set by the diagnostic pulse intensity setting adjuster (235) at an intensity suitable for achieving a fluorescent image of cancer-related gene expression pattern.

The irradiation extent setting adjuster (239) sets an extent in which living cells are irradiated with pulsed laser light. The operation controller (233) controls the operations of the two-dimensional scanner (217) and the focal depth controller (223), thereby irradiating pulsed laser light at the set irradiation extent and depth and condensing it. The irradiation time setting adjuster (241) sets the time for irradiating pulse laser light on living cells. Then, the operation controller (233) controls the output of the laser oscillator (213) so that pulse laser light is emitted for a set time.

In an embodiment, the controller (231) has a storage unit (51) and a determination unit (52). That is, the cancer testing device (201) determines the malignancy and prognosis of malignant transformation of a living cell group in real time based on the staining state of the living cell group in the images achieved by photographing.

By using the cancer testing device (201), the malignancy of malignant transformation is determined based on staining state of cancer-related gene expression pattern of living cell groups, so that the malignant transformation of the living cell groups can be grasped at an early stage. Further, since the malignancy of malignant transformation can be grasped by the expression state of cancer-related genes, the prognosis of cancer patients can be known.

The cancer testing device (201) is equipped with a treatment pulse intensity setting adjuster (237), so that a pulse laser beam intensity that is high enough to destroy living cells for performing a treatment can be set. Accordingly, early cancer treatment can be performed on the cancer cell population discovered.

In addition, the cancer test device (201) can be used in various forms.

Figure 15:
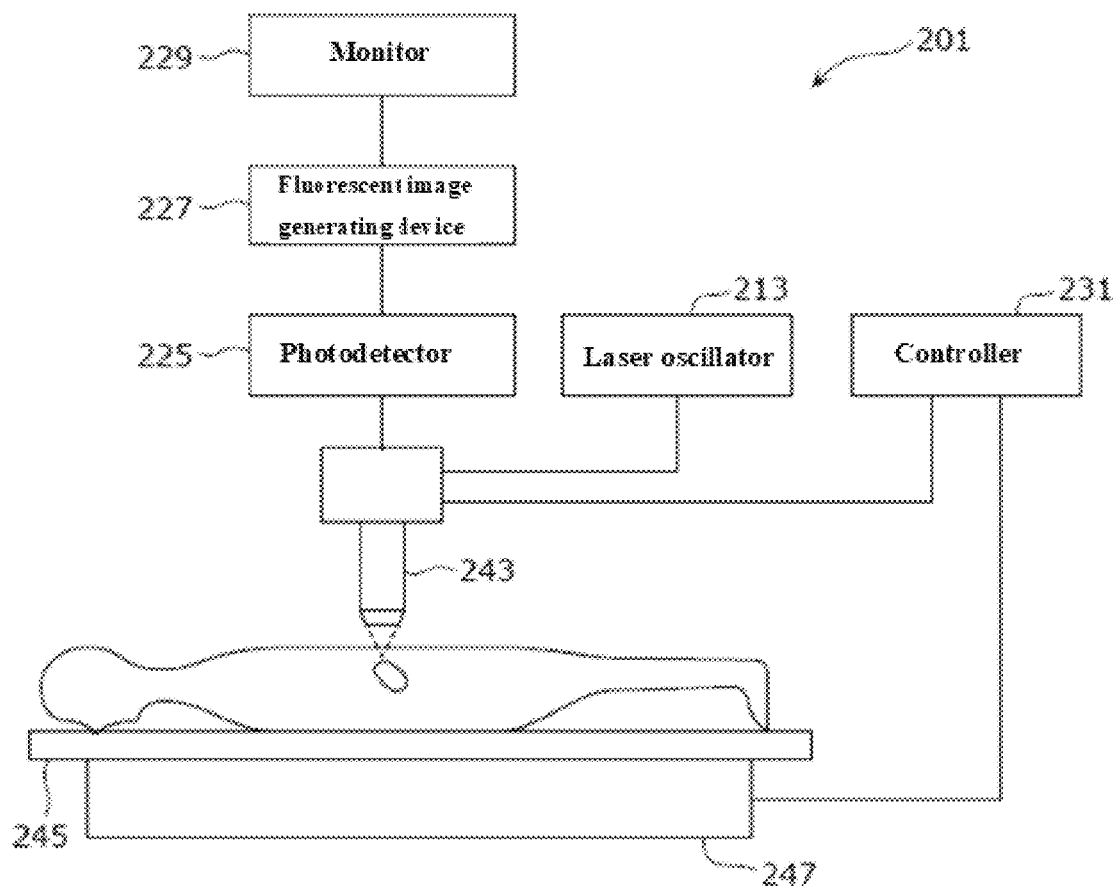
FIG. 15 illustrates a cancer test.

For example, as shown in FIG. 15, to perform a cancer test, beam diameter controller (215), two-dimensional scanner (217), an optical system consisting of a dichroic mirror (219), objective lens (221) and an optical path therebetween, and focal depth controller (223) are provided in the laser irradiation head (243), and a patient fixing table (245) for mounting a patient together with a moving device (247) are further provided.

Besides, for example, the malignancy of malignant transformation may also be determined from images taken with the cancer test device (201) when the shaved living cell group is placed in a tray (sample stage) after being scrapped off a part of a living cell group from a patient. In this case, coating the stain 45 to a living cell group may be performed before the living cell group is scraped, or may be performed after the living cell group is scraped but before photographing. In addition, the cancer testing device can also be used to accurately cut out the affected area of cancer in real time during surgery, or to show that it was cut out accurately after resection. When used for surgery, an accurate position in cm units is known in advance by a normal endoscope, CT, X-ray imaging, or the like in order to specify a site on which surgery is to be performed. By using the cancer testing device of the present invention at the time of surgery, the boundary between cancer tissues and normal tissues can be accurately grasped. It is possible to remove a cancer radically while minimizing the extent of tissue removal, which significantly reduces the burden on patients undergoing cancer removal surgery.

Specifically, as described with reference to the schematic diagrams of FIG. 8 to FIG. 13, after staining in advance with curcumin or the like, the confirmation can be made on the monitor (229), or can be notified by sound such as a buzzer or by light such as a flash or a color light from an alarm. The effect in this case is that the boundary between normal cells and early cancer parts can be clearly determined from images from the center of an advanced cancer. It can be determined instantaneously whether it is an early cancer cell, a normal cell, a neuronal cell, a blood vessel, or a noise from the fluorescence intensity, fluorescence color and shape of cell (nucleus, crypt, etc.). Accordingly, as described above, marking the margins of cancer tissues is greatly supportive to a surgeon. In this case, a surgical thread or tape may be used as the biometric marking for surgery, or a marking dye may be used. However, it is particularly useful to provide a nozzle for marking dye in conjunction with the objective lens (221) in FIG. 14. In addition, it is also effective to increase laser irradiation intensity to partially burn peripheral contour of cancer tissue or to evaporate it into a shape shown in dashed line.

In determining the peripheral portion, the movable portion including the objective lens of the cancer testing device (201) is moved in the X-Y direction by a distance including the peripheral portion of a cancer center, and the point where the fluorescence density mostly decreases is marked. Thereafter, by rotating the movable portion at an angle of, for example, about 5 degrees and repeating the same moving sweep, the outermost peripheral edge portion to be resected including the advanced cancer can be marked.

As described above, the present invention provides a method for identifying tissues and cells necessary for a surgeon to immediately make a pathological diagnosis decision during surgery, thereby enabling radical resection of a cancer while reducing the extent of tissue removal. As a result, the burden on patients undergoing cancer removal surgery is greatly reduced.

The invention claimed is:

1. A method for detecting cancer progression comprising staining an organ tissue suspected of having cancer with curcumin and then laser irradiating the organ tissue from serosal side or lumen using a multiphoton laser microscopic endoscope, confocal laser microscopic endoscope or laser fluorescent microscopic endoscope, and visualizing Meissner's plexus or Auerbach's plexus present in the organ tissue, wherein the organ tissue is digestive tract tissue, and a primary lesion is in mucosal epithelium.

2. The method according to claim 1, wherein if cancer cells have invaded or reached Meissner's plexus, the cancer is an advanced cancer.

3. The method according to claim 1, wherein if cancer cells have invaded or reached the Meissner's plexus and smooth muscle layer, the cancer is an advanced cancer.

4. The method according to claim 1, wherein if cancer cells have not invaded or reached Meissner's plexus, the cancer is an early cancer.

5. The method according to claim 1, which further comprises signaling the detection of cancer cells by sound or light.

6. A method of claim 1 for treating cancer patients comprising removing cancer cells one by one from serosal side or lumen.

7. A method of claim 1 for removing the cancer cells one-by-one, comprising confirming cancer cells remaining in a living body from serosal side or lumen after surgery.

8. A method according to claim 1 for treating colon cancer patients.

9. A method according to claim 1 for treating lung cancer patients.

10. A method according to claim 1 for treating prostate cancer patients.

11. A method according to claim 1 for treating gastric cancer patients.

12. A method according to claim 1 for treating esophageal cancer patients.

13. A method according to claim 1 for treating bladder cancer patients.

14. A method according to claim 1 for diagnosing advanced cancer, wherein the cancer is judged as an advanced cancer based on visualized images if the cancer cells have invaded or reached Meissner's plexus, or the cancer cells have invaded or reached Meissner's plexus and smooth muscle layer.

15. A method according to claim 1 for diagnosing early cancer, wherein the cancer is judged as an early cancer based on visualized images if the cancer cells have not invaded or reached Meissner's plexus.

16. A method according to claim 1 for treating patients with uterine cancer or ovarian cancer.

17. A method according to claim 1 for treating patients with breast cancer.

18. A method according to claim 1 for treating patients with pancreatic cancer or gallbladder cancer.

19. A method according to claim 1 for treating tongue cancer, throat cancer, laryngeal cancer, or thyroid cancer.

* * * * *